United States Patent
Belosludtsev et al.

(10) Patent No.: US 12,173,019 B2
(45) Date of Patent: Dec. 24, 2024

(54) PROTEIN PROXIMITY ASSAY IN FORMALIN FIXED PAFFAFIN EMBEDDED TISSUE USING CAGED HAPTENS

(71) Applicant: Ventana Medical Systems, Inc., Tucson, AZ (US)

(72) Inventors: Yuri Belosludtsev, Tucson, AZ (US); Traci D. DeGeer, Tucson, AZ (US); Wendy J. French, Oro Valley, AZ (US); Junshan Hao, Tucson, AZ (US); Brian Daniel Kelly, Tucson, AZ (US); Adrian Murillo, Tucson, AZ (US); Nathan Walter Polaske, Oracle, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 276 days.

(21) Appl. No.: 17/345,072

(22) Filed: Jun. 11, 2021

(65) Prior Publication Data

US 2021/0309680 A1 Oct. 7, 2021

Related U.S. Application Data

(63) Continuation of application No. 15/907,479, filed on Feb. 28, 2018, now Pat. No. 11,053,266, which is a (Continued)

(51) Int. Cl.
*G01N 33/542* (2006.01)
*C07F 9/6558* (2006.01)
(Continued)

(52) U.S. Cl.
CPC ....... *C07F 9/65583* (2013.01); *G01N 33/542* (2013.01); *G01N 33/573* (2013.01); *G01N 33/58* (2013.01)

(58) Field of Classification Search
CPC .. C07F 9/65583; G01N 33/58; G01N 33/573; G01N 33/542
See application file for complete search history.

(56) References Cited

U.S. PATENT DOCUMENTS

| 5,424,440 A | 6/1995 | Klem et al. |
| 5,614,368 A | 3/1997 | Ghazarossian et al. |

(Continued)

FOREIGN PATENT DOCUMENTS

| CN | 102762971 A | 10/2012 |
| CN | 103513039 A | 1/2014 |

(Continued)

OTHER PUBLICATIONS

English translation of Official Action for JP2019-511411, issued on Aug. 3, 2021.
(Continued)

*Primary Examiner* — Shafiqul Haq
(74) *Attorney, Agent, or Firm* — Charney IP Law LLC; Thomas M. Finetti

(57) ABSTRACT

Disclosed herein are caged haptens and caged hapten-antibody conjugates useful for enabling the detection of targets located proximally to each other in a sample.

19 Claims, 16 Drawing Sheets
(13 of 16 Drawing Sheet(s) Filed in Color)

Related U.S. Application Data continuation of application No. PCT/US2016/049153, filed on Aug. 26, 2016.

(60) Provisional application No. 62/301,489, filed on Feb. 29, 2016, provisional application No. 62/211,590, filed on Aug. 28, 2015.

(51) Int. Cl.
*G01N 33/573* (2006.01)
*G01N 33/58* (2006.01)

(56) References Cited

U.S. PATENT DOCUMENTS

| | | | |
|---|---|---|---|
| 11,053,266 | B2 | 7/2021 | Belosludtsev et al. |
| 2003/0235877 | A1 | 12/2003 | Kohl et al. |
| 2006/0040319 | A1* | 2/2006 | Muir ............ C07K 14/47 435/7.1 |
| 2008/0220434 | A1 | 9/2008 | Thomas |
| 2016/0002701 | A1 | 1/2016 | Farrell et al. |
| 2016/0187326 | A1 | 6/2016 | Dose et al. |
| 2018/0186821 | A1 | 7/2018 | Belosludtsev et al. |
| 2019/0233447 | A1 | 8/2019 | Belosludtsev et al. |

FOREIGN PATENT DOCUMENTS

| | | | |
|---|---|---|---|
| CN | 103561772 A | 2/2014 | |
| CN | 105738612 A | 7/2016 | |
| JP | 2003247944 A | 9/2003 | |
| JP | 2014517842 A | 7/2014 | |
| JP | 2016512324 A | 4/2016 | |
| JP | 6880001 B2 | 6/2021 | |
| WO | 1990000618 A1 | 1/1990 | |
| WO | 2003014698 A2 | 2/2003 | |
| WO | 2005099768 A2 | 10/2005 | |
| WO | 2009018003 A2 | 2/2009 | |
| WO | 2011064701 A1 | 6/2011 | |
| WO | 2012162482 A1 | 11/2012 | |
| WO | WO-2014139980 A1 * | 9/2014 | ............ C12Q 1/25 |
| WO | 2015088930 A1 | 6/2015 | |
| WO | 2015124703 A1 | 8/2015 | |
| WO | 2015153401 A1 | 10/2015 | |
| WO | 2016083364 A1 | 6/2016 | |
| WO | 2017040349 A1 | 3/2017 | |

OTHER PUBLICATIONS

Antczak, C. et al., A New Acivicin Prodrug Designed for Tumor-Targeted Delivery, Bioorg Med Chem, (2001), pp. 2843-2848, vol. 9 Issue 11.

Burke, et al., Recent Advances in the development of synthetic chemical probes for glycosidase enzymes, ChemComm, 2012, pp. 10576-10588, vol. 51.

Chen S. et al., Identification of Interaction Protein with FAM3A, J Sun Yat-sen Univ (Med Sci), (2008), pp. 521-525, with EN-Abstract, vol. 29.

Hong, R. et al., In Situ Detection of Protein Complexes and Modifications by Chemical Ligation Proximity Assay, Bioconjugate Chemistry, (2016), pp. 1690-1696, vol. 27 No. 7.

Hongmei Zhang et A., An enzyme-activatable probe with a self-immolative linker for rapid and sensitive alkaline phosphatase detection and cell imaging through a cascade reaction, Chemical Communications, (2015), pp. 7031-7034, vol. 52 No. 32.

International Search Report, Issued Dec. 23, 2016, in Application No. PCT/US 16/49153, 5 pages.

Martin, R. Bruce, Reactions of Carbonyl Compounds with Amines and Derivatives, The Journal of Physical Chemistry, Jun. 1964, pp. 1369-1377, vol. 68, No. 6.

Stanford, et al, pCAP-Based Peptide Substrates: The New Tool in the Box of, Methods, 2014, pp. 165-174, vol. 65.

Szychowski et al., 2008, "Cleavable Biotin Probes for Labeling of Biomolecules via Azide-Alkyme Cycloaddition," Journal of the American Chemical Society, 132:18351-18360.

Zhao, R Y et al, Synthesis and Biological Evaluation of Antibody Conjugates of Phosphate Prodrugs of Cytotoxic DNA Alkylators for the Targeted Treatment of Cancer, J Med Chem, (2012), pp. 766-782, vol. 55 Issue 2.

* cited by examiner

Native (uncaged) HQ hapten

Caged HQ hapten

PSA on Prostate tissue (A) Caged hapten + AP (B) Caged hapten - AP (C) Native (uncaged) hapten

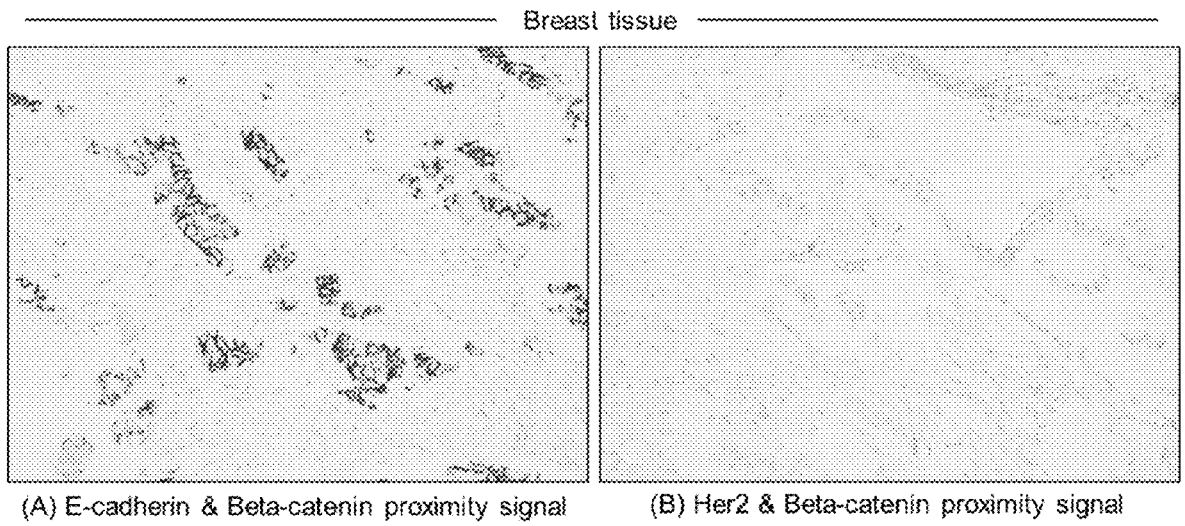
(A) E-cadherin & Beta-catenin proximity signal
FIG. 9A
(B) Her2 & Beta-catenin proximity signal
FIG. 9B
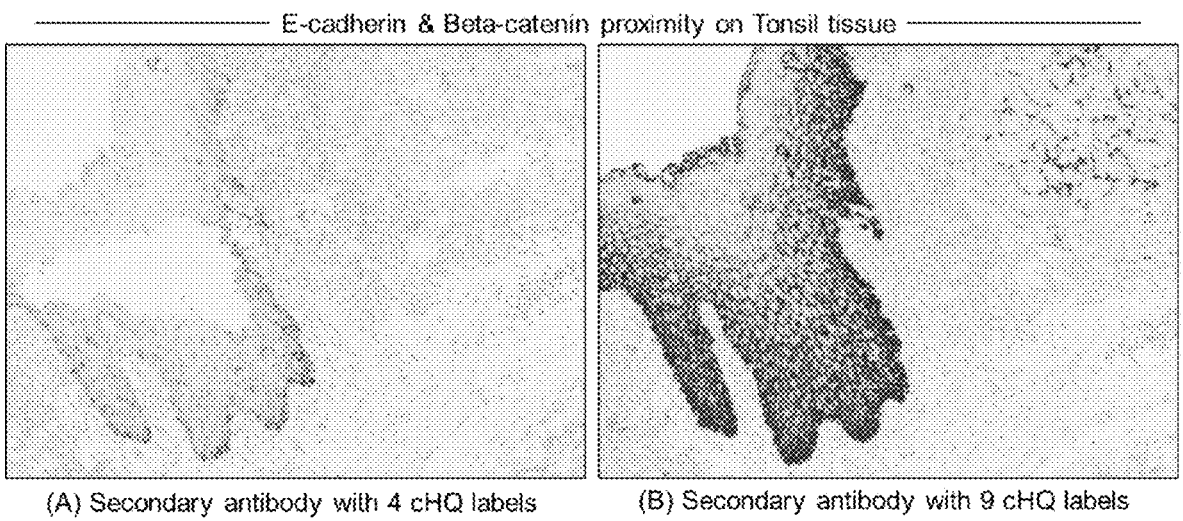
(A) Secondary antibody with 4 cHQ labels
FIG. 10A
(B) Secondary antibody with 9 cHQ labels
FIG. 10B

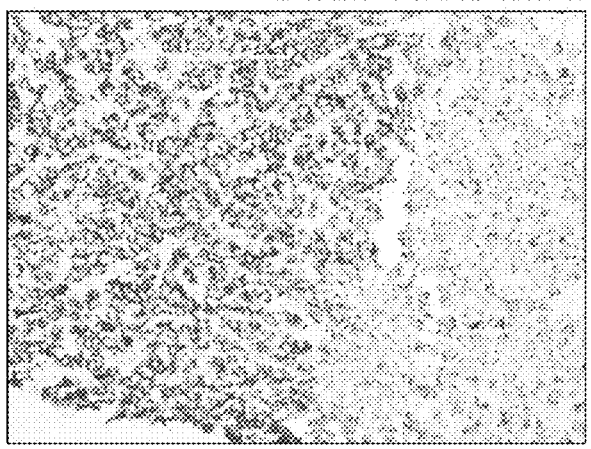 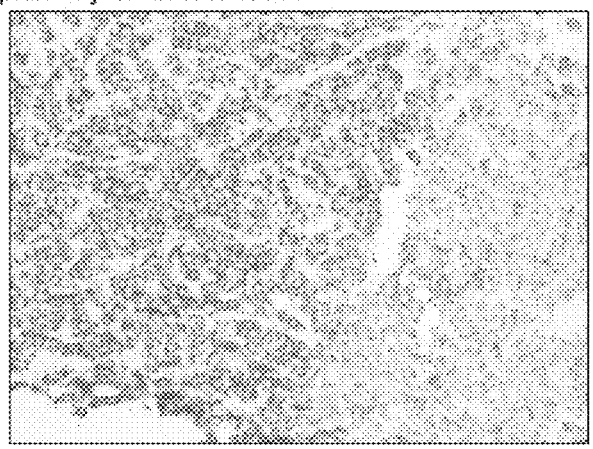
FIG. 11A  FIG. 11B

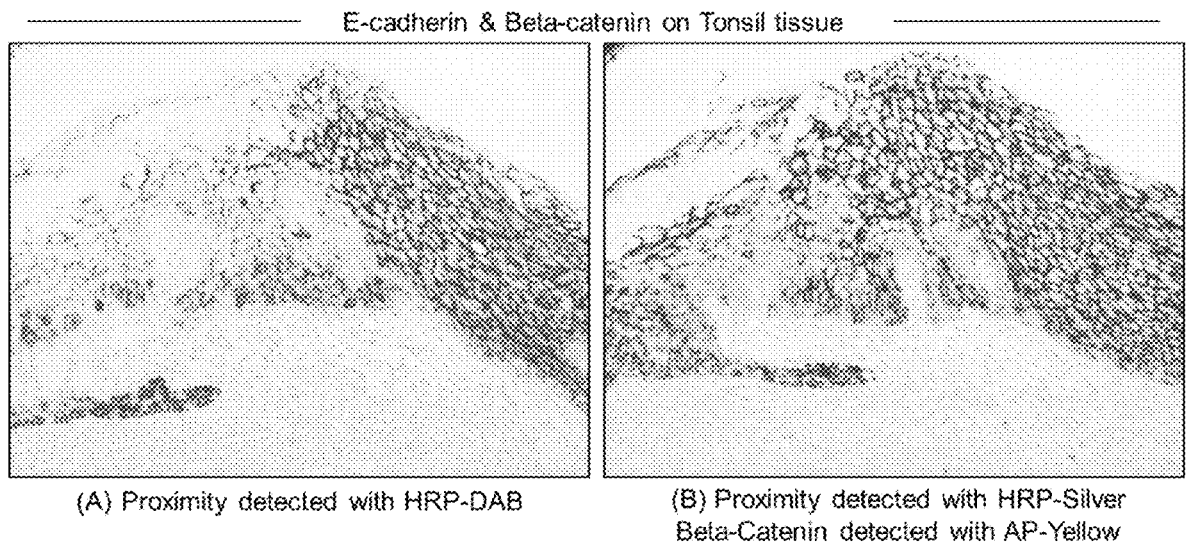
(A) Proximity detected with HRP-DAB
(B) Proximity detected with HRP-Silver
Beta-Catenin detected with AP-Yellow
FIG. 13A     FIG. 13B
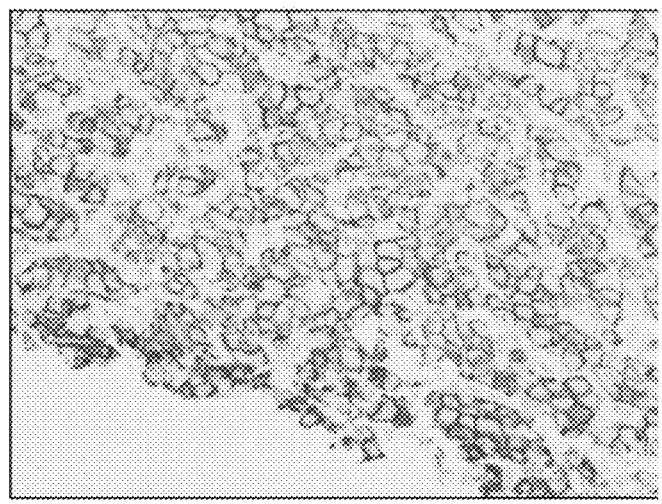
Proximity detected with HRP-Purple
Beta-Catenin detected with AP-Yellow
FIG. 14

PROTEIN PROXIMITY ASSAY IN FORMALIN FIXED PAFFAFIN EMBEDDED TISSUE USING CAGED HAPTENS

CROSS REFERENCE TO RELATED APPLICATIONS

The present application is a continuation of U.S. patent application Ser. No. 15/907,479 filed on Feb. 28, 2018, which application is a continuation of International Application PCT/US2016/049153 filed on Aug. 26, 2016, which application claims the benefit of the filing date of U.S. Provisional Patent Application No. 62/301,489 filed Feb. 29, 2016, and the benefit of the filing date of U.S. Provisional Patent Application No. 62/211,590 filed Aug. 28, 2015, the disclosures of which are hereby incorporated herein by reference in their entireties.

FIELD OF THE INVENTION

Disclosed embodiments concern detecting targets in a sample, including targets located proximally in a sample. Disclosed embodiments also provide for a proximity assay for detecting protein dimers in formalin-fixed, paraffin embedded tissue using caged haptens or caged hapten conjugates.

STATEMENT OF INDUSTRIAL APPLICABILITY

The present disclosure has industrial applicability in the fields of chemistry and diagnostics.

BACKGROUND OF THE INVENTION

Immunohistochemistry (IHC) refers to the processes of detecting, localizing, and/or quantifying antigens, such as a protein, in a biological sample using antibodies specific to the particular antigens. IHC provides the substantial advantage of identifying exactly where a particular protein is located within the tissue sample. It is also an effective way to examine the tissues themselves. In situ hybridization (ISH) refers to the process of detecting, localizing, and quantifying nucleic acids. Both IHC and ISH can be performed on various biological samples, such as tissue (e.g. fresh frozen, formalin fixed, paraffin embedded) and cytological samples. Recognition of the targets can be detected using various labels (e.g., chromogenic, fluorescent, luminescent, radiometric), irrespective of whether the target is a nucleic acid or an antigen. To robustly detect, locate, and quantify targets in a clinical setting, amplification of the recognition event is desirable as the ability to confidently detect cellular markers of low abundance becomes increasingly important for diagnostic purposes. For example, depositing at the marker's site hundreds or thousands of label molecules in response to a single antigen detection event enhances, through amplification, the ability to detect that recognition event.

Networks of protein-protein interactions are the hallmarks of biological systems. Protein-protein interactions form signal pathways that regulate all aspects of cellular functions in normal and cancerous cells. Methods have been developed for detecting protein-protein interactions, such as transient receptor tyrosine kinase dimerization and complex formation after extracellular growth factor activation; however, these methods are not particularly designed to be used on formalin fixed paraffin embedded (FFPE) tissues.

The ability to interrogate for presence and distribution of specific intermolecular interactions for biomarkers known to be important determinants in cancer biology is of high interest in the context of new diagnostic capabilities and for determining therapeutic effect in the context of pharmaceutical development. The ability to probe and document distributions of molecular interactions on frozen and paraffin embedded tissue has remained inaccessible; alternative technologies to approach this question have been proposed, although the solutions have not proven to be effective and reliable under practical use.

A proximity ligation assay has recently been developed by OLink AB. This is the only known commercial product for in situ detection of protein-protein interactions on formalin fixed paraffin embedded tissue. Proximity ligation assay technology uses DNA ligases to generate a padlock circular DNA template, as well as Phi29 DNA polymerase for rolling circle amplification. These enzymes are expensive. Moreover, these enzymes are not amenable for use with automated systems and methods. For these reasons, proximity ligation assays are not considered generally useful for commercial applications.

BRIEF SUMMARY OF THE INVENTION

Applicants have developed a superior method of detecting targets located proximally in a sample. In one aspect of the present disclosure is a method for analyzing a sample to determine whether a first target is proximal to a second target, the method comprising: (a) forming a second target-unmasking enzyme-antibody conjugate complex; (b) forming a first target-caged hapten-antibody conjugate complex; (c) unmasking the caged hapten of the first target-caged hapten-antibody conjugate complex to form a first target-unmasked hapten-antibody conjugate complex; (d) contacting the sample with first detection reagents to label the first target-unmasked hapten-antibody conjugate complex or the first target; and (e) detecting the labeled first target-unmasked hapten-antibody conjugate complex or labeled first target.

In some embodiments, the first detection reagents comprise (i) a secondary antibody specific to the unmasked hapten of the first target-unmasked hapten-antibody complex, the secondary antibody conjugated to a first enzyme such that the secondary antibody labels the first target-unmasked hapten-antibody complex with the first enzyme; and (ii) a first substrate for the first enzyme. In some embodiments, the first substrate is a chromogenic substrate or a fluorescent substrate. In some embodiments, the first detection reagents include amplification components to label the unmasked enzyme of the first target-unmasked hapten-antibody conjugate complex with a plurality of first reporter moieties. In some embodiments, the plurality of first reporter moieties are haptens. In some embodiments, the first detection reagents further comprise secondary antibodies specific to the plurality of first reporter moieties, each secondary antibody conjugated to a second reporter moiety. In some embodiments, the second reporter moiety is selected from the group consisting of an amplification enzyme or a fluorophore. In some embodiments, the second reporter moiety is an amplification enzyme and wherein the first detection reagents further comprise a first chromogenic substrate or a fluorescent substrate for the amplification enzyme. In some embodiments, the method further comprises contacting the sample with a second substrate specific for the unmasking enzyme of the second target-unmasking enzyme-antibody conjugate complex and detecting signals corresponding to a product of a reaction between the second substrate and the unmasking enzyme.

In another aspect of the present disclosure is a method for analyzing a sample to determine whether a first target is proximal to a second target, the method comprising: (a) forming a second target-unmasking enzyme-antibody conjugate complex; (b) forming a first target-caged hapten-antibody conjugate complex; (c) unmasking the caged hapten of the first target-caged hapten-antibody conjugate complex to form a first target-unmasked hapten-antibody conjugate complex; (d) performing a signal amplification step to label the first target-unmasked hapten-antibody conjugate complex with a plurality of reporter moieties; and (e) detecting the plurality of reporter moieties.

In some embodiments, the plurality of reporter moieties are haptens; and wherein the method further comprises introducing secondary antibodies specific to the plurality of first reporter moieties, each secondary antibody conjugated to a second reporter moiety. In some embodiments, the second reporter moiety is an amplification enzyme and wherein the method further comprises introducing a chromogenic substrate or a fluorescent substrate for the amplification enzyme. In some embodiments, the method further comprises detecting a total amount of target in the sample.

In another aspect of the present disclosure is a method for analyzing a sample to determine whether a first target is proximal to a second target, the method comprising: (a) forming a second target-unmasking enzyme-antibody conjugate complex; (b) forming a first target-caged hapten-antibody conjugate complex; (c) performing a decaging step such that an unmasking enzyme of the second target-unmasking enzyme-antibody conjugate complex reacts with an enzyme substrate portion of the first target-caged hapten-antibody conjugate complex to form a first target-unmasked hapten-antibody conjugate complex; (d) contacting the sample with first detection reagents to label the first target-unmasked hapten-antibody conjugate complex or the first target; and (e) detecting the labeled first target-unmasked hapten-antibody conjugate complex or labeled first target.

In some embodiments, the decaging step comprises changing the temperature of the sample. In some embodiments, the decaging step comprises altering a pH of the sample. In some embodiments, the decaging step comprises introducing one or more washing steps. In some embodiments, the decaging step comprises adding cofactors for the unmasking enzyme. In some embodiments, the method further comprises detecting a total amount of target in the sample.

In another aspect of the present disclosure is a method for analyzing a sample to determine whether a first target is proximal to a second target, the method comprising: (a) contacting the sample with a caged hapten-antibody conjugate specific to the first target to form a first target-caged hapten-antibody conjugate complex; (b) contacting the sample with an unmasking enzyme-antibody conjugate specific to the second target to form a second target-unmasking enzyme-antibody conjugate complex, wherein an unmasking enzyme of the unmasking enzyme-antibody conjugate is selected such that it is capable of reacting with an enzyme substrate portion of the caged hapten-antibody conjugate to form a first target-unmasked hapten-antibody conjugate complex; (c) contacting the sample with first detection reagents to label the first target-unmasked hapten-antibody conjugate complex or the first target; and (d) detecting the labeled first target-unmasked hapten-antibody conjugate complex or labeled first target.

In some embodiments, a caged hapten portion of the caged hapten-antibody conjugate is derived from a hapten selected from the group consisting of DCC, biotin, nitropyrazole, thiazolesulfonamide, benzofurazan, and 2-hydroxyquinoxaline. In some embodiments, the unmasking enzyme of the unmasking enzyme-antibody conjugate is selected from the group consisting of alkaline phosphatase, B-glucosidase, B-Galactosidase, B-Glucuronidase, Lipase, Sulfatase, Amidase, Protease, Nitroreductase, beta-lactamase, neuraminidase, and Urease. In some embodiments, the first detection reagents comprise (i) a secondary antibody specific to the unmasked hapten of the first target-unmasked hapten-antibody complex, the secondary antibody conjugated to a first enzyme such that the secondary antibody labels first target-unmasked hapten-antibody complex with the first enzyme; and (ii) a first chromogenic substrate or fluorescent substrate. In some embodiments, the first enzyme is different than the unmasking enzyme. In some embodiments, the first enzyme is a peroxidase. In some embodiments, the first chromogenic substrate is selected from the group consisting of 3,3'-diaminobenzidine (DAB), 3-amino-9-ethylcarbazole (AEC), HRP-Silver, and tyramide-chromogens. In some embodiments, the method further comprises contacting the sample with a second chromogenic substrate or fluorescent substrate specific for the unmasking enzyme of the second target-unmasking enzyme-antibody conjugate complex, wherein the first and second chromogenic substrates are different. In some embodiments, the first detection reagents include components to amplify the amount of label introduced to the first target-unmasked hapten-antibody conjugate complex. In some embodiments, the first target is one of PD-1 or PD-L1, and the second target is the other of PD-1 or PD-L1.

In another aspect of the present disclosure is a method for analyzing a sample to determine whether a first target is proximal to a second target, the method comprising: (a) contacting the sample with a first detection probe, the first detection probe comprising one of a caged hapten-antibody conjugate or an unmasking enzyme-antibody conjugate; (b) contacting the sample with a second detection probe, the second detection probe comprising the other of the caged hapten-antibody conjugate or the unmasking enzyme-antibody conjugate; (c) contacting the sample with at least first detection reagents to label a formed unmasked hapten-antibody conjugate target complex; (d) detecting signals from the labeled unmasked hapten-antibody conjugate target complex.

In some embodiments, the method further comprises detecting a total amount of target within the sample. In some embodiments, the first detection reagents include amplification components to label the unmasked enzyme of the first target-unmasked hapten-antibody conjugate complex with a plurality of first reporter moieties. In some embodiments, the plurality of first reporter moieties are haptens. In some embodiments, the first detection reagents further comprise secondary antibodies specific to the plurality of first reporter moieties, each secondary antibody conjugated to a second reporter moiety. In some embodiments, the second reporter moiety is selected from the group consisting of an amplification enzyme or a fluorophore. In some embodiments, the second reporter moiety is an amplification enzyme and wherein the first detection reagents further comprise a first chromogenic substrate or fluorescent substrate for the amplification enzyme. In some embodiments, the method further comprises a decaging step.

In another aspect of the present disclosure is a method for analyzing a sample to determine whether a first target is proximal to a second target, the method comprising: (a) contacting the sample with a caged hapten-antibody conjugate specific to the first target to form a first target-caged hapten-antibody conjugate complex; (b) contacting the sample with an unmasking enzyme-antibody conjugate specific to the second target to form a second target-unmasking enzyme-antibody conjugate complex, wherein an unmasking enzyme of the unmasking enzyme-antibody conjugate is selected such that it is capable of reacting with an enzyme substrate portion of the caged hapten-antibody conjugate to form a first target-unmasked hapten-antibody conjugate complex; (c) contacting the sample with a first labeling conjugate that specifically binds to the first target-unmasked hapten-antibody conjugate complex, wherein the first labeling conjugate comprises a first enzyme which differs from the unmasking enzyme; (d) contacting the sample with a first signaling conjugate comprising a first latent reactive moiety and a first chromogenic or fluorescent moiety; and (e) detecting signals from the first chromogenic or fluorescent moiety, the first signals being indicative of proximal first and second targets.

In some embodiments, the method further comprises contacting the sample with a second signaling conjugate comprising a second latent reactive moiety and a second chromogenic or fluorescent moiety, wherein the first and second chromogenic or fluorescent moieties provide different signals. In some embodiments, further comprises detecting signals from the second chromogenic moiety, the signals from the second chromogenic or fluorescent moiety being indicative of total protein.

In another aspect of the present disclosure is a caged hapten having Formula (I):

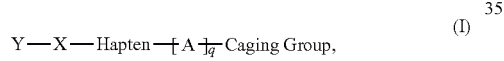

wherein
Y is selected from a carbonyl-reactive group, an amine-reactive group, or a thiol-reactive group;
X is a bond, or a group comprising a branched or unbranched, substituted or unsubstituted, saturated or unsaturated aliphatic group having between 1 and 30 carbon atoms, and optionally having one or more heteroatoms selected from the group consisting of O, N, or S;
A is a bond, or a group comprising a branched or unbranched, substituted or unsubstituted, saturated or unsaturated aliphatic group having between 1 and 15 carbon atoms, and optionally having one or more heteroatoms selected from the group consisting of O, N, or S; and
'Caging Group' comprises an enzyme substrate and optionally a leaving group, wherein the leaving group portion comprises a substituted or unsubstituted 5-, 6-, or 7-membered aromatic or heterocyclic ring.

In some embodiments, the 5-, 6-, or 7-membered aromatic or heterocyclic ring is substituted with a moiety selected from the group consisting of a halogen, a —S-alkyl group having between 1 and 4 carbon atoms; an —O-alkyl group having between 1 and 4 carbon atoms; a —N(H)-alkyl group having between 1 and 4 carbon atoms; a —N-(alkyl)$_2$ group having between 1 and 6 carbon atoms; and a branched or unbranched, substituted or unsubstituted alkyl group having between 1 and 4 carbon atoms. In some embodiments, the caging group has the structure of Formula (II):

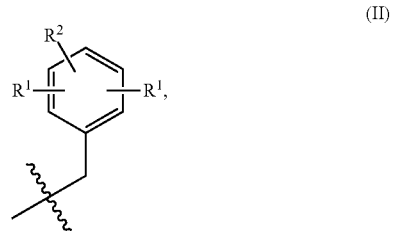

wherein
$R^1$ is independently selected from H, F, Cl, Br, I, —O-methyl, —O-ethyl, —O-n-propyl, —O-iso-propyl; —O-n-butyl, —O-sec-butyl, or —O-iso-butyl; a —S-alkyl group having between 1 and 4 carbon atoms; an —O-alkyl group having between 1 and 4 carbon atoms; a —N(H)-alkyl group having between 1 and 4 carbon atoms; a —N-(alkyl) 2 group having between 1 and 6 carbon atoms; an alkyl group having between 1 and 4 carbon atoms and optionally substituted with N or S; cyano groups; and carboxyl groups; and
$R^2$ is an enzyme substrate.

In some embodiments, the enzyme substrate is selected from the group consisting of a phosphate group, an ester group, an amide group, a sulfate group, a glycoside group, a urea group, and a nitro group. In some embodiments, the caging group has the structure of Formula (IIB):

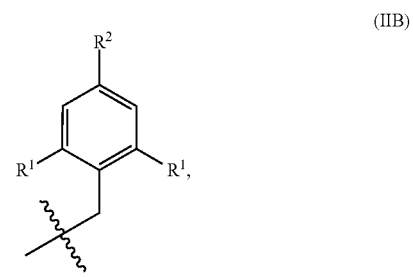

and
wherein $R^2$ is selected from the group consisting of a phosphate group, an ester group, an amide group, a sulfate group, a glycoside group, a urea group, and a nitro group. In some embodiments, each $R^1$ group is different.

In some embodiments, the caging group has the structure of Formula (IIC):

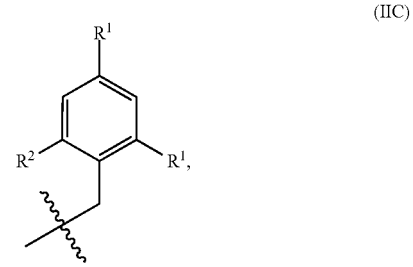

and
wherein $R^2$ is selected from the group consisting of a phosphate group, an ester group, an amide group, a sulfate group, a glycoside group, a urea group, and a nitro group. In some embodiments, each $R^1$ group is different.

In some embodiments, the caging group has the structure of Formula (IID):

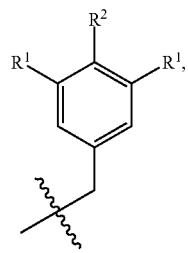

and wherein $R^2$ is selected from the group consisting of a phosphate group, an ester group, an amide group, a sulfate group, a glycoside group, a urea group, and a nitro group.

In some embodiments, each $R^1$ group is different. In some embodiments, X has the structure of Formula (IIIA):

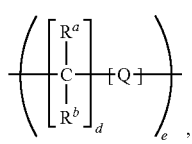

wherein d and e are integers each independently ranging from 4 to 18; Q is a bond, O, S, or $N(R^c)(R^d)$; $R^a$ and $R^b$ are independently H, a $C_1$-$C_4$ alkyl group, F, Cl, or $N(R^c)(R^d)$; and $R^c$ and $R^d$ are independently $CH_3$ or H. In some embodiments, d and e are integers each independently ranging from 1 to 24.

In some embodiments, the caged hapten is selected from the group consisting of:

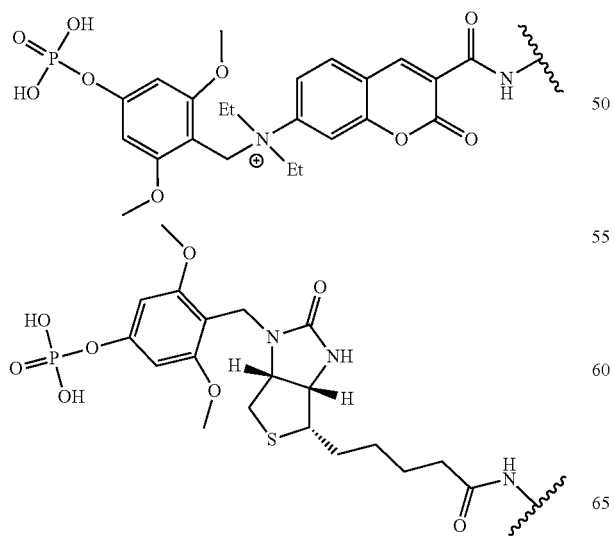

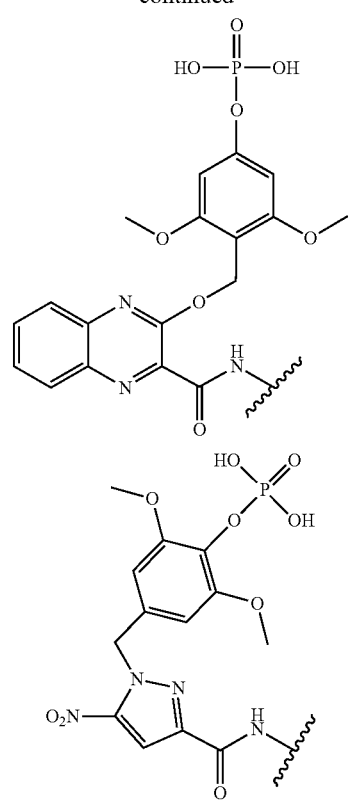

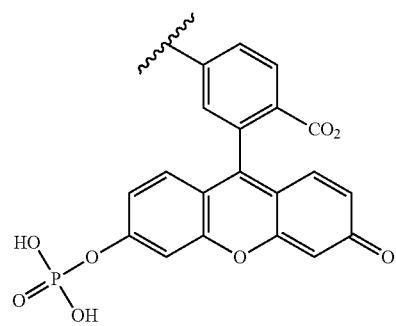

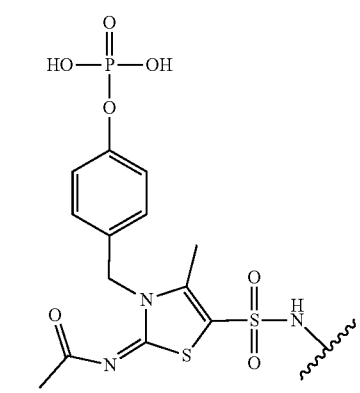

-continued

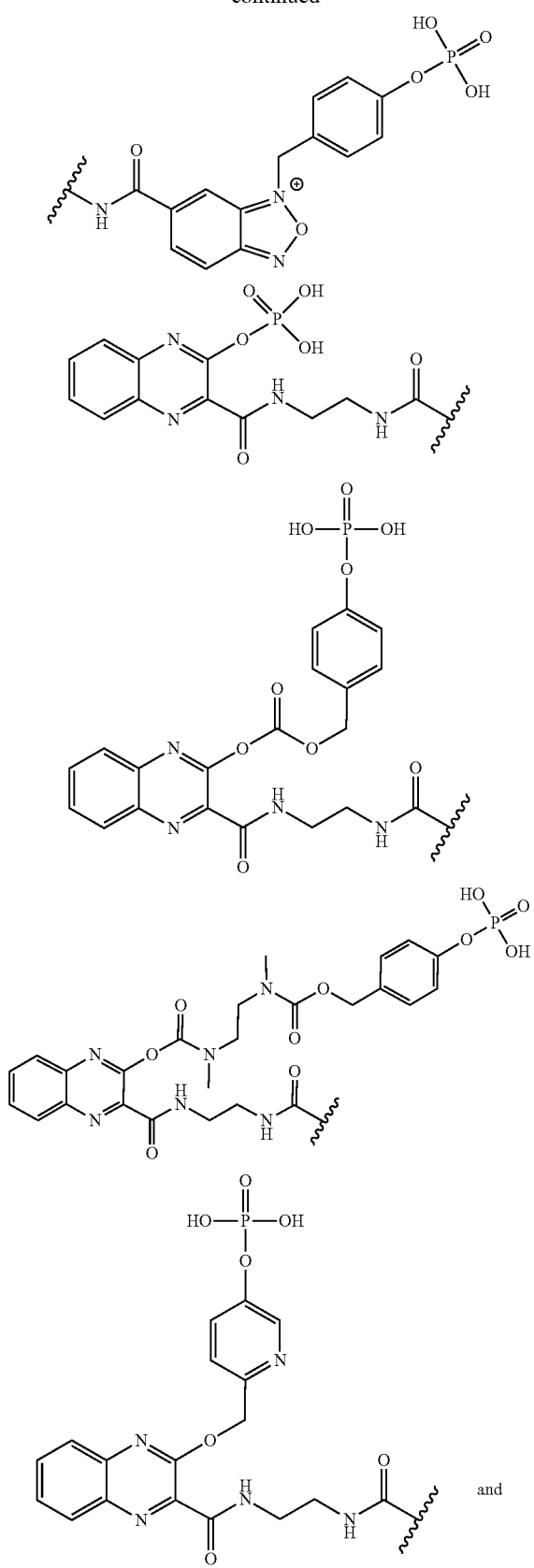

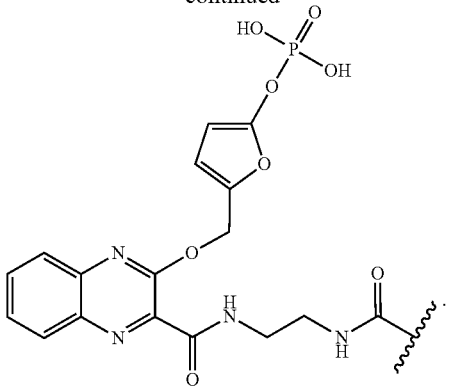

and

-continued

In another aspect of the present disclosure is a conjugate of (i) a specific binding entity, and (ii) a caged hapten, including any of the caged haptens cited herein. In some embodiments, the caged hapten has the structure of Formula (I):

$$Y-X-\text{Hapten}-[A]_q-\text{Caging Group} \quad (I)$$

wherein
Y is selected from a carbonyl-reactive group, an amine-reactive group, or a thiol-reactive group;
X is a bond, or a group comprising a branched or unbranched, substituted or unsubstituted, saturated or unsaturated aliphatic group having between 1 and 30 carbon atoms, and optionally having one or more heteroatoms selected from the group consisting of O, N, or S;
A is a bond, or a group comprising a branched or unbranched, substituted or unsubstituted, saturated or unsaturated aliphatic group having between 1 and 15 carbon atoms, and optionally having one or more heteroatoms selected from the group consisting of O, N, or S; and
'Caging Group' comprises an enzyme substrate and optionally a leaving group, wherein the leaving group portion comprises a substituted or unsubstituted 5-, 6-, or 7-membered aromatic or heterocyclic ring.

In some embodiments, the specific binding entity of the conjugate is an antibody. In some embodiments, the conjugate has the structure of Formula (IV):

$$\text{Antibody}-[Z-\text{Hapten}-[A]_q-\text{Caging Group}]_n, \quad (IV)$$

wherein Z is a bond, or a group comprising a branched or unbranched, substituted or unsubstituted, saturated or unsaturated aliphatic group having between 1 and 30 carbon atoms, and optionally having one or more heteroatoms selected from the group consisting of O, N, or S,
A is a bond, or a group comprising a branched or unbranched, substituted or unsubstituted, saturated or unsaturated aliphatic group having between 1 and 15 carbon atoms, and optionally having one or more heteroatoms selected from the group consisting of O, N, or S;

q is 0 or 1; and n is an integer ranging from 1 to 25.

In some embodiments, the caging group is a 5-, 6-, or 7-membered aromatic or heterocyclic ring optionally substituted with a moiety selected from the group consisting of a halogen, a —S-alkyl group having between 1 and 4 carbon atoms; an —O-alkyl group having between 1 and 4 carbon atoms; a —N(H)-alkyl group having between 1 and 4 carbon atoms; a —N-(alkyl) 2 group having between 1 and 6 carbon atoms; and a branched or unbranched, substituted or unsubstituted alkyl group having between 1 and 4 carbon atoms.

In some embodiments, the caging group has the structure of Formula (II):

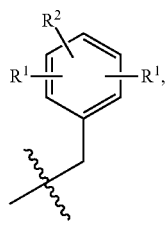

(II)

wherein $R^1$ is independently selected from H, F, Cl, Br, I, —O-methyl, —O-ethyl, —O-n-propyl, —O-iso-propyl; —O-n-butyl, —O-sec-butyl, or —O-iso-butyl; a —S-alkyl group having between 1 and 4 carbon atoms; an —O-alkyl group having between 1 and 4 carbon atoms; a —N(H)-alkyl group having between 1 and 4 carbon atoms; a —N-(alkyl) 2 group having between 1 and 6 carbon atoms; an alkyl group having between 1 and 4 carbon atoms and optionally substituted with N or S; cyano groups; and carboxyl groups; and $R^2$ is an enzyme substrate.

In some embodiments, the enzyme substrate is selected from the group consisting of a phosphate group, an ester group, an amide group, a sulfate group, a glycoside group, a urea group, and a nitro group.

In some embodiments, the caging group has the structure of Formula (IIB):

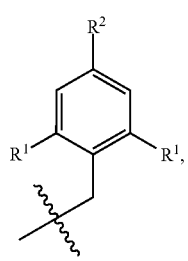

(IIB)

and wherein $R^2$ is selected from the group consisting of a phosphate group, an ester group, an amide group, a sulfate group, a glycoside group, a urea group, and a nitro group. In some embodiments, each $R^1$ group is different.

In some embodiments, the caging group has the structure of Formula (IIC):

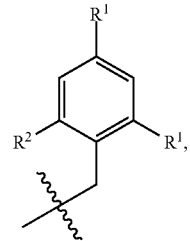

(IIC)

and wherein $R^2$ is selected from the group consisting of a phosphate group, an ester group, an amide group, a sulfate group, a glycoside group, a urea group, and a nitro group. In some embodiments, $R^1$ group is different.

In some embodiments, the caging group has the structure of Formula (IID):

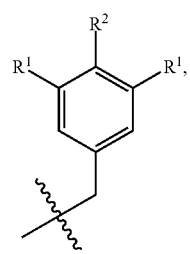

(IID)

and wherein $R^2$ is selected from the group consisting of a phosphate group, an ester group, an amide group, a sulfate group, a glycoside group, a urea group, and a nitro group. In some embodiments, each $R^1$ group is different.

In some embodiments, the antibody is a secondary antibody. In some embodiments, the antibody is a primary antibody. In some embodiments, the primary antibody is specific for a target selected from the group consisting of PD-L1/CD80 (B7-1); CTLA-4/CD80 (B7-1); CTLA-4/CD86 (B7-1); PD-L2/PD-1; any combination of a ErbB family (Her1 (EGFR), Her2, Her3, Her4); any combination of DNA mixed match repair proteins (MLH1, MLH3, MSH2, MSH3, MSH6, PMS1 and PMS2); post translational modifications (PTM)-phosphorylated proteins (combining an anti-phosphotyrosine/phosphoserine/phosphothreonine/phosphohistidine antibody with any antibody specific against the target in question); and PTM-ubiquitinated proteins.

In another aspect of the present disclosure is a method for detecting multiple targets within a sample comprising: (a) contacting the sample with a caged hapten-antibody conjugate specific to the first target to form a first target-caged hapten-antibody conjugate complex; (b) contacting the sample with an unmasking enzyme-antibody conjugate specific to the second target to form a second target-unmasking enzyme-antibody conjugate complex, wherein an unmasking enzyme of the unmasking enzyme-antibody conjugate is selected such that it is capable of reacting with an enzyme substrate portion of the caged hapten-antibody conjugate to form a first target-unmasked hapten-antibody conjugate complex; (c) contacting the sample with first detection reagents to label the first target-unmasked hapten-antibody conjugate complex or the first target; (d) contacting the sample with a first detection probe specific to a third target to form a third target-detection probe complex; (e) contacting the sample with second detection reagents to label the third target-detection probe complex; (f) detecting the labeled first target-unmasked hapten-antibody conjugate complex or labeled first target; and (g) detecting the labeled third target-detection probe complex. In some embodiments, the method further comprises detecting total protein within the sample. In some embodiments, the first detection probe comprises an antibody. In some embodiments, the first detection probe comprises a nucleic acid probe. In some embodiments, the method further comprised contacting the sample with a second detection probe specific to a fourth target to form a fourth target-detection probe complex. In some embodiments, the method further comprises inactivating the unmasking enzyme prior to contacting the sample with second detection reagents. In some embodiments, the method further comprises inactivating the first and second target complexes prior to contacting the sample with a probe to label the third target and second detection reagents.

BRIEF DESCRIPTION OF THE FIGURES

The patent or application file contains at least one drawing executed in color. Copies of this patent or patent application publication with color drawings will be provided to the Office upon request and the payment of the necessary fee.

FIG. 9A is an image of co-localized proteins with proximity as measured with DAB staining on FFPE breast tissue.

FIG. 9B is an additional image of co-localized proteins without proximity as measured by the absence of DAB staining on FFPE breast tissue.

FIG. 10A is an image of signal intensity based on the number of caged hapten labels on the secondary antibody.

FIG. 10B is an additional image of the increase in signal intensity based on the increased number of caged hapten labels on the secondary antibody.

FIG. 11A is an image of proximity signal detection as measured with HRP-Silver staining.

FIG. 11B is an additional image of proximity signal detection as measured with HRP-Purple chromogen staining.

FIG. 13A is an image demonstrating detection of proximal proteins with HRP-DAB.

FIG. 13B is an image demonstrating detection of proximal proteins with HRP-Silver and total protein with AP-Yellow.

FIG. 14 is an image demonstrating detection of the proximity signal using HRP-Purple and total protein using AP-Yellow.

DETAILED DESCRIPTION

Figure 1A:
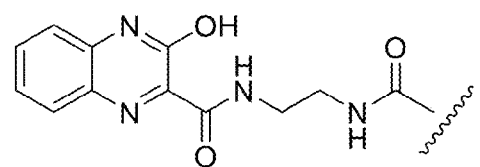
FIG. 1A illustrates an embodiment of an unmasked hapten.

Disclosed herein are caged haptens and their method of synthesis. Also disclosed herein are conjugates comprising a caged hapten. As will be described in more detail herein, the caged hapten conjugates may be used to detect proximal antigens in tissue samples. These and other embodiments are described herein.

Definitions

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, alkaline phosphatase (AP) is an enzyme that removes (by hydrolysis) and transfers phosphate group organic esters by breaking the phosphate-oxygen bond, and temporarily forming an intermediate enzyme-substrate bond. For example, AP hydrolyzes naphthol phosphate esters (a substrate) to phenolic compounds and phosphates. The phenols couple to colorless diazonium salts (chromogen) to produce insoluble, colored azo dyes.

As used herein, the term "antibody," occasionally abbreviated "Ab," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the phrase "antibody conjugates," refers to those antibodies conjugated (either directly or indirectly) to one or more labels, where the antibody conjugate is specific to a particular target and where the label is capable of being detected (directly or indirectly), such as with a secondary antibody (an anti-label antibody). For example, an antibody conjugate may be coupled to a hapten such as through a polymeric linker and/or spacer, and the antibody conjugate, by means of the hapten, may be indirectly detected. As an alternative example, an antibody conjugate may be coupled to a chromogen, such as through a polymeric linker and/or spacer, and the antibody conjugate may be detected directly. Antibody conjugates are described further in US Publication No. 2014/0147906 and U.S. Pat. Nos. 8,658,389; 8,686,122; 8,618,265; 8,846,320; and 8,445,191. By way of a further example, the term "antibody conjugates" includes those antibodies conjugated to an enzyme, e.g. HRP or AP.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules s such as complex carbohydrates (e.g., polysaccharides), phospholipids, nucleic acids and proteins.

As used herein, the term a "biological sample" can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In certain examples, a sample is a quality control sample, such as one of the disclosed cell pellet section samples. In other examples, a sample is a test sample. Samples can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Samples can include multiple targets that can be specifically bound by one or more detection probes.

As used herein, the term "chromophore" refers to a molecule or a part of a molecule (e.g. a chromogenic substrate) responsible for its color. Color arises when a molecule absorbs certain wavelengths of visible light and transmits or reflects others. A molecule having an energy difference between two different molecular orbitals falling within the range of the visible spectrum may absorb visible light and thus be aptly characterized as a chromophore. Visible light incident on a chromophore may be absorbed thus exciting an electron from a ground state molecular orbital into an excited state molecular orbital.

As used herein, the term "conjugate" refers to two or more molecules or moieties (including macromolecules or supramolecular molecules) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules moieties.

As used herein, the terms "couple" or "coupling" refers to the joining, bonding (e.g. covalent bonding), or linking of one molecule or atom to another molecule or atom.

As used herein, the term "detectable moiety" refers to a molecule or material that can produce a detectable (such as visually, electronically or otherwise) signal that indicates the presence (i.e. qualitative analysis) and/or concentration (i.e. quantitative analysis) of the label in a sample. A detectable signal can be generated by any known or yet to be discovered mechanism including absorption, emission and/or scattering of a photon (including radio frequency, microwave frequency, infrared frequency, visible frequency and ultraviolet frequency photons). Examples of detectable moieties include chromogenic, fluorescent, phosphorescent and luminescent molecules and materials.

As used herein, the term "epitopes" refers to an antigenic determinant, such as continuous or non-continuous peptide sequences on a molecule that are antigenic, i.e. that elicit a specific immune response. An antibody binds to a particular antigenic epitope.

As used herein, horseradish peroxidase (HRP) is an enzyme that can be conjugated to a labeled molecule. It produces a colored, fluorometric, or luminescent derivative of the labeled molecule when incubated with a proper substrate, allowing it to be detected and quantified. HRP acts in the presence of an electron donor to first form an enzyme substrate complex and then subsequently acts to oxidize an electronic donor. For example, HRP may act on 3,3'-diaminobenzidine hydrochloride (DAB) to produce a detectable color. HRP may also act upon a labeled tyramide conjugate, or tyramide like reactive conjugates (i.e. ferulate, coumaric, caffeic, cinnamate, dopamine, etc.), to deposit a colored or fluorescent or colorless detectable moiety for tyramide signal amplification (TSA).

As used herein, the terms "multiplex," "multiplexed," or "multiplexing" refer to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

As used herein, the term "primary antibody" refers to an antibody which binds specifically to the target protein antigen in a tissue sample. A primary antibody is generally the first antibody used in an immunohistochemical procedure.

As used herein, the term "secondary antibody" herein refers to an antibody which binds specifically to a primary antibody, thereby forming a bridge between the primary antibody and a subsequent reagent (e.g. a label, an enzyme, etc.), if any. The secondary antibody is generally the second antibody used in an immunohistochemical procedure.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4$ $M^{-1}$ greater or $10^5$ $M^{-1}$ greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

As used herein, the term "target" refers to any molecule for which the presence, location and/or concentration is or can be determined. Examples of target molecules include proteins, epitopes, nucleic acid sequences, and haptens, such as haptens covalently bonded to proteins. Target molecules are typically detected using one or more conjugates of a specific binding molecule and a detectable label.

As used herein, the terms "tyramide signal amplification" or "TSA" refer to an enzyme-mediated detection method that utilizes the catalytic activity of a peroxidase (such as horseradish peroxidase) to generate high-density labeling of a target molecule (such as a protein or nucleic acid sequence) in situ. TSA typically involves three basic steps: (1) binding of a specific binding member (e.g., an antibody) to the target followed by secondary detection of the specific binding member with a second peroxidase-labeled specific binding member; (2) activation of multiple copies of a labeled tyramide derivative (e.g., a hapten-labeled tyramide) by the peroxidase; and (3) covalent coupling of the resulting highly reactive tyramide radicals to residues (e.g., the phenol moiety of protein tyrosine residues) proximal to the peroxidase-target interaction site, resulting in deposition of haptens proximally (diffusion and reactivity mediated) to the target. In some examples of TSA, more or fewer steps are involved; for example, the TSA method can be repeated sequentially to increase signal. Methods of performing TSA and commercial kits and reagents for performing TSA are available (see, e.g., AmpMap Detection Kit with TSA™, Cat. No. 760-121, Ventana Medical Systems, Tucson, Ariz.; Invitrogen; TSA kit No. T-20911, Invitrogen Corp, Carlsbad, Calif.). Other enzyme-catalyzed, hapten or signaling linked reactive species can be alternatively used as they may become available.

Caged Haptens

Figure 1B:
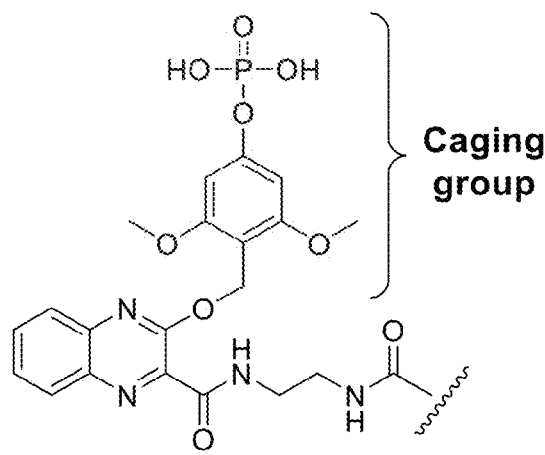
FIG. 1B illustrates an embodiment of a caged hapten.
Figure 1C:
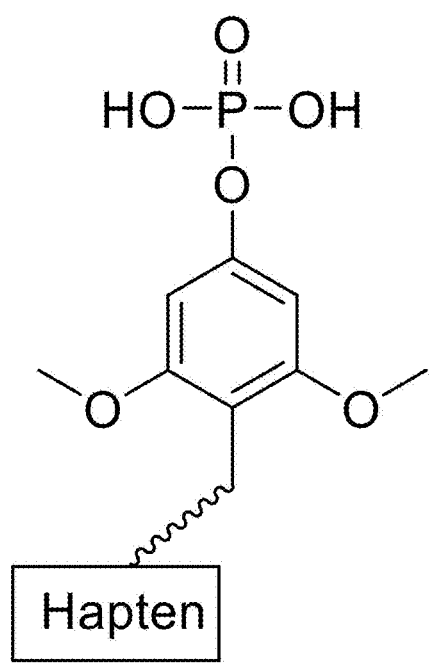
FIG. 1C illustrates a structure of a caging group coupled to a hapten.

In one aspect of the present disclosure are "caged haptens," such as illustrated in FIG. 1B. As those of skill in the art will appreciate, haptens are small molecules that anti-hapten antibodies have been raised against. A "caged hapten" is a hapten whose structure has been modified such that a suitable anti-hapten antibody no longer recognizes the molecule and no binding event occurs. In effect, the hapten's identity is "masked" or "protected." The caged haptens disclosed herein have been designed with an enzyme cleavable cage such that the respective hapten, i.e. the un-caged or unmasked hapten, is released by enzymatic treatment to regenerate the native hapten (see, for example, FIG. 2, which illustrates the unmasking of a caged hapten via enzymatic treatment). Thus, in the presence of an appropriate enzyme, the caged hapten is unmasked and an anti-hapten antibody is free to bind to it.

In some embodiments, the caged haptens of the present disclosure have the structure of Formula (I):

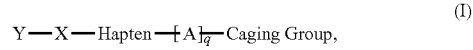

(I)

wherein
- X is a bond, or a group comprising a branched or unbranched, substituted or unsubstituted, saturated or unsaturated aliphatic group having between 1 and 30 carbon atoms, and optionally having one or more heteroatoms selected from the group consisting of O, N, or S;
- A is a group comprising a branched or unbranched, substituted or unsubstituted, saturated or unsaturated aliphatic group having between 1 and 15 carbon atoms, and optionally having one or more heteroatoms selected from the group consisting of O, N, or S;
- Y is a reactive group capable of forming a covalent bond with another group; and
- "hapten" and "Caging Group" are as described herein; and
- q is 0 or 1.

In some embodiments, the caging group is an enzyme cleavable moiety comprised of two covalently bonded components, namely (i) a leaving group portion, and (ii) an enzyme substrate portion, as illustrated in Formula (IA).

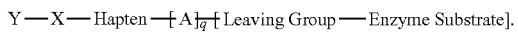
(IA)

In other embodiments, the caging group comprises only an enzyme substrate, coupled directly or indirectly to the hapten as in Formula (IB):

(IB)

Examples of suitable enzyme substrates (and the enzymes that act upon them) include, but are not limited to, phosphate groups (acted upon by an alkaline phosphatase), ester groups (acted upon by a lipase); sulfate groups (acted upon by a sulfatase); glycoside groups (acted upon by a glycosylase); amide groups (acted upon by an amidase or a protease); urea groups (acted upon by a urease); and nitro groups (acted upon by a nitroreductase).

In some embodiments, the leaving group comprises a 5-, 6-, or 7-membered aromatic ring or heterocyclic ring, where any position of the ring may be substituted or unsubstituted. In some embodiments, the leaving group is a substituted or unsubstituted 5-, 6-, or 7-membered heterocyclic ring having one, two, or three heteroatoms selected from O, N, or S. In some embodiments, the leaving group is selected from a substituted or unsubstituted furan, pyrrole, thiophene, imidazole, pyrazole, oxazole, isoxazole, thiazole, pyridine, pyrazine, pyrimidine, pyridazine, a triazine, 2H-pyran, 4H-pyran, 2H-thiopyran, 4H-thiopyran, an oxazine, or a thiazine. In some embodiments, the 5-, 6-, or 7-membered aromatic or heterocyclic ring is substituted with a halogen, a —S-alkyl group having between 1 and 4 carbon atoms; an —O-alkyl group having between 1 and 4 carbon atoms; a —N(H)-alkyl group having between 1 and 4 carbon atoms; a —N-(alkyl) 2 group having between 1 and 6 carbon atoms; or a branched or unbranched, substituted or unsubstituted alkyl group having between 1 and 4 carbon atoms which itself may comprise one or more heteroatoms selected from O, N, or S and/or which may be substituted with one or more halogens. In some embodiments, the leaving group may be substituted with a nitro group, a cyano group, or a carboxy group.

In some embodiments, the caging group has the structure of Formula (II):

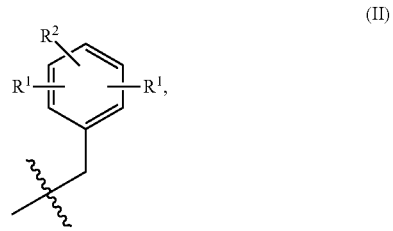
(II)

wherein
- each $R^1$ is independently selected from H, F, Cl, Br, I, —O-methyl, —O-ethyl, —O-n-propyl, —O-iso-propyl; —O-n-butyl, —O-sec-butyl, or —O-iso-butyl; a —S-alkyl group having between 1 and 4 carbon atoms; an —O-alkyl group having between 1 and 4 carbon atoms; a —N(H)-alkyl group having between 1 and 4 carbon atoms; a —N-(alkyl) 2 group having between 1 and 6 carbon atoms; an alkyl group having between 1 and 4 carbon atoms and optionally substituted with N or S; cyano groups; and carboxyl groups.
- $R^2$ is an enzyme substrate.

In some embodiments, each $R^1$ group is the same. In other embodiments, each $R^1$ group is different (i.e. each $R^1$ comprises a different moiety). For example, a first $R^1$ group may comprise a halogen while a second $R^1$ may comprise an alkyl group.

While Formula (II) depicts a six-membered aromatic ring comprising six carbon atoms, the skilled artisan will appreciate that one or more heteroatoms (e.g. O, N, or S) may be substituted for one or more of the carbon atoms of the aromatic ring.

In some embodiments, the ability of any leaving group to leave depends on the electronics of the hapten. In some embodiments, the electronics of certain haptens require electron donating groups to encourage leaving group ability. In other embodiments, the haptens require an electron withdrawing group. For example, depending on the pKa of the functional group being caged, some haptens require the addition of electron donating groups on the leaving group of the caging group, while others may require electron withdrawing groups. Without wishing to be bound by any particular theory, is believed that hapten functional groups with a high pKa value tend to require electron donating groups. This is most likely because once the leaving group is expelled, the electron donating groups in this position are able to directly stabilize the resulting positive charge of the leaving group through inductive or resonance effects. An example of this was seen in the caged-HQ, where in the absence of electron donating groups, the leaving group would not leave without excessively high reaction temperature (about 100° C.). On the other hand, it is believed that for hapten functional groups with a low pKa value, electron withdrawing groups may be required. This is most likely because the once the leaving group is expelled, the resulting negative charge on the hapten functional group has such high stability that a destabilizing electronic force may be necessary on the leaving group to help stabilize the caged hapten against hydrolysis. It is believed that an electron withdrawing group could destabilize the positive charge on the leaving group, thereby making the caged hapten more stable toward hydrolysis.

The substituents $R^1$ and $R^2$ may be located at any position along the ring of Formula (II) relative to the group coupling the Caging Group to the hapten. In some embodiments, $R^2$ is positioned para to the group coupling the Caging Group to the hapten, such as illustrated in Formula (IIA):

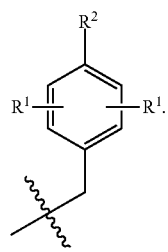

(IIA)

In other embodiments of the compounds of Formula (IIA), the substituents $R^1$ may independently be positioned ortho or meta to group $R^2$. In some embodiments, each $R^1$ group of Formula (IIA) is different, i.e. each $R^1$ group comprises a different moiety.

In further embodiments, the Caging Group has the structure of Formula (IIB):

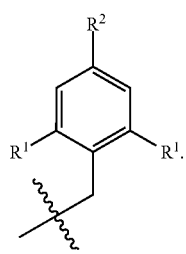

(IIB)

In some embodiments, each $R^1$ group of Formula (IIB) is different, i.e. each $R^1$ group comprises a different moiety.

In yet further embodiments, the Caging Group has the structure of Formula (IIC):

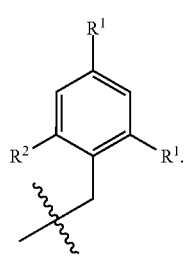

(IIC)

In some embodiments, each $R^1$ group of Formula (IIC) is different, i.e. each $R^1$ group comprises a different moiety.

In yet further embodiments, the Caging Group has the structure of Formula (IID):

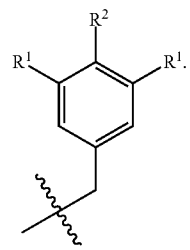

(IID)

In some embodiments, each $R^1$ group of Formula (IID) is different, i.e. each $R^1$ group comprises a different moiety.

Without wishing to be bound by any particular theory, it is believed that the hydrolytic stability and leaving group ability of the caging group can be different when coupled to different haptens. For example, the caging group with —OMe groups installed at the meta position relative to the phosphate are believed to provide a good mix of stability and reactivity on a 2-hydroxyquinoxaline (HQ) hapten, but were believed to be comparatively less stable than desired when installed on the nitropyrazole (NP) hapten. This was remedied by using a caging group with —OMe groups installed ortho relative to the phosphate group. Again, without wishing to be bound by any particular theory, it was believed that the O-benzyl bond formed between the HQ hapten and the caging group was much more stable than the N-benzyl bond formed between the NP and the caging group. This was similarly remedied by introducing a —OMe group ortho to the benzyl group on the HQ hapten to help "push" the electrons through the ring and break the bond, once the phosphate was cleaved. The NP hapten was comparatively less stable, and therefore it did not require the same "push."

Again, and without wishing to be bound by any particular theory, it is believed that a caging group with no-OMe groups may require very high temperatures to disassemble. However, a caging group with —OMe groups ortho to the phosphate may require moderate temperature to disassemble; while a caging group with the —OMe meta to the phosphate group may be able to disassemble at room temperature. Without wishing to be bound by any particular theory, it is believed that it may be possible to add stability while also increasing reactivity by adding one or two additional aliphatic groups to the benzyl position. It is believed that this may sterically protect the benzyl group from hydrolysis, while also creating a more stable 2° or 3° benzyl carbocation upon disassembly.

Figure 2:
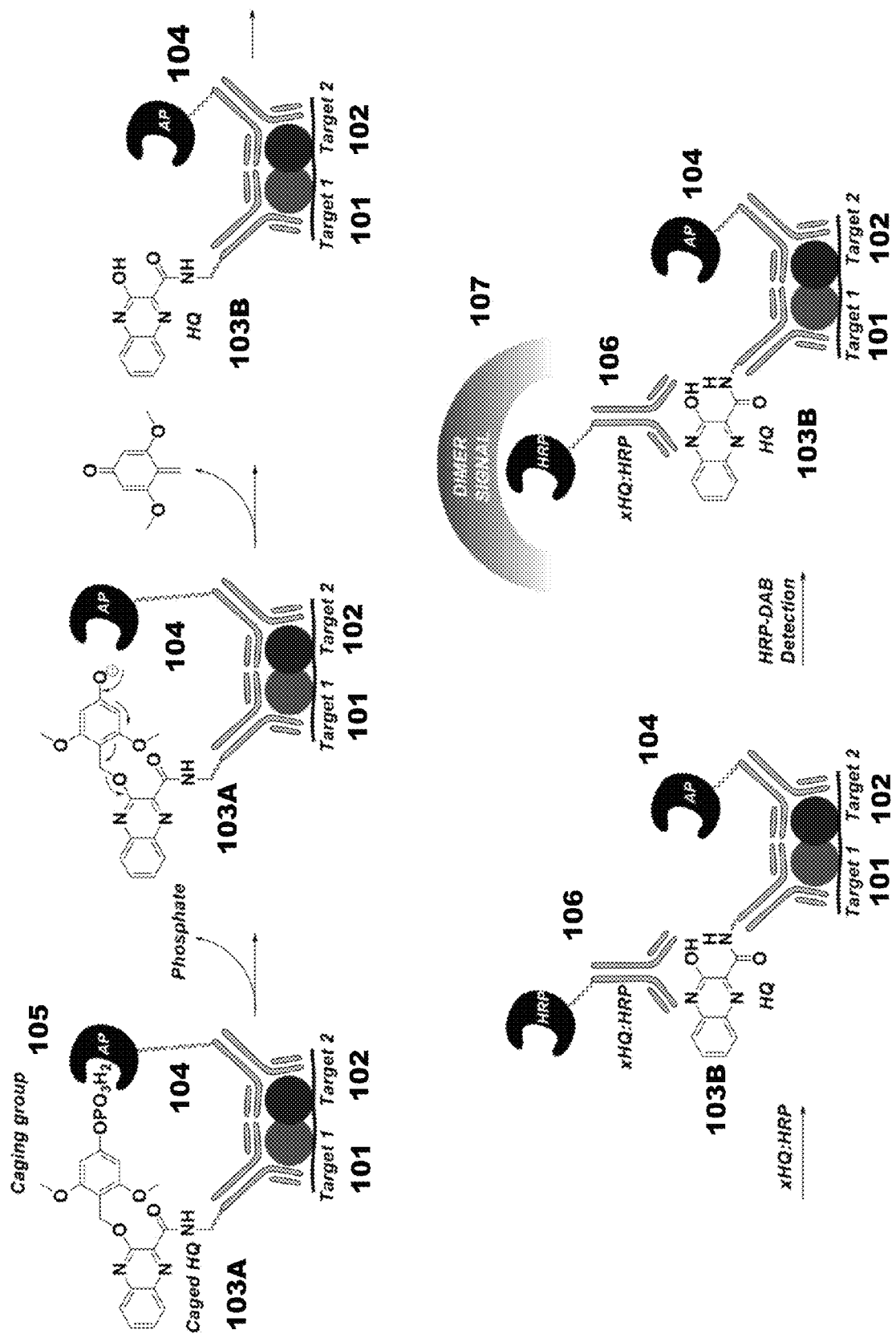
FIG. 2 is a schematic illustrating the interaction between an unmasking enzyme-antibody conjugate comprising an alkaline phosphatase (bound to Target 2) and a caged hapten-antibody conjugate (bound to Target 1), where the unmasking enzyme of the unmasking enzyme-antibody conjugate reacts with an enzyme substrate portion of the caged hapten-antibody conjugate (by virtue of the proximity of Target 1 and Target 2 to each other) to provide the respective unmasked hapten, which may be detected.

As noted herein, upon interaction of an enzyme with the enzyme substrate portion of the caging group, the caging group undergoes an electronic change such that the Caging Group separates from the caged hapten, resulting in an un-caged hapten or un-masked hapten. FIG. 2 illustrates the electronic changes that occur within a caged HQ hapten upon interaction of an alkaline phosphatase enzyme with the phosphate enzyme substrate portion of the caging group. Similar electronic changes occur in other caged hapten systems as will be appreciated by those of ordinary skill in the art.

In some embodiments, haptens include, but are not limited to, pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives; oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triperpenes; and cyclolignans.

Specific examples of haptens include di-nitrophenyl, biotin, digoxigenin, and fluorescein, and any derivatives or analogs thereof. Other haptens are described in U.S. Pat. Nos. 8,846,320; 8,618,265; 7,695,929; 8,481,270; and 9,017,954, the disclosures of which are incorporated herein by reference in their entirety.

As noted above, X may a bond; or a group comprising a branched or unbranched, substituted or unsubstituted, saturated or unsaturated aliphatic group having between 1 and 30 carbon atoms, and optionally having one or more heteroatoms selected from the group consisting of O, N, or S. In some embodiments, X may comprise carbonyl, amine, ester, ether, amide, imine, thione or thiol groups. In other embodiments, X may comprise one or more terminal groups selected from an amine, a carbonyl, ester, ether, amide, imine, thione, or thiol.

In some embodiments, X has the structure of Formula (IIIA):

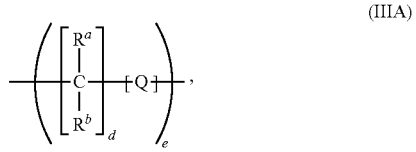

wherein d and e are integers each independently ranging from 4 to 18; Q is a bond, O, S, or $N(R^c)(R^d)$; $R^a$ and $R^b$ are independently H, a $C_1$-$C_4$ alkyl group, F, Cl, or $N(R^c)(R^d)$; and $R^c$ and $R^d$ are independently $CH_3$ or H. In some embodiments, d and e are integers each independently ranging from 1 to 24.

In other embodiments, the X has the structure depicted in Formula (IIIB):

wherein d and e are integers each independently ranging from 1 to 24; Q is a bond, O, S, or $N(R^c)(R^d)$; and $R^c$ and $R^d$ are independently $CH_3$ or H. In other embodiments, Q is O.

In yet other embodiments, the 'Linker' has the structure depicted in Formula (IIIC):

wherein d and e are integers each independently ranging from 1 to 24. In some embodiments, d is 2 and e ranges from 2 through 24.

In yet other embodiments, X may include one or more alkylene oxide or PEG groups (e.g. PEG2 through PEG24). A person of ordinary skill in the art will appreciate that, as the number of oxygen atoms increases, the hydrophilicity of the compound also may increase.

Without wishing to be bound by any particular theory, it is believed that the linker length may affect the proximity signal. For example, caged haptens comprising PEG8, PEG4 and no PEG linkers were made and tested. The longer in length the linker was, the more signal we saw on our control dimer system of E-cad and B-cat. While "more signal" may seem like it would always be useful, in this case it was not because we also observed signal when testing on protein markers that co-localize but are known to not form dimers (Ki67 and Bcl6). We found that using no PEG linker eliminated the signal on the co-localized control system while still providing some signal on the known dimer control system. As a result, some caged hapten embodiments do not include a PEG group.

As noted herein, A is a group comprising a branched or unbranched, substituted or unsubstituted, saturated or unsaturated aliphatic group having between 1 and 15 carbon atoms, and optionally having one or more heteroatoms selected from the group consisting of O, N, or S. In some embodiments, A has the structure of Formula (IIID):

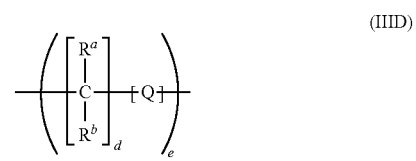

wherein d and e are integers each independently ranging from 2 to 15; Q is a bond, O, S, or $N(R^c)(R^d)$; $R^a$ and $R^b$ are independently H, a $C_1$-$C_4$ alkyl group, F, Cl, or $N(R^c)(R^d)$; and $R^c$ and $R^d$ are independently $CH_3$ or H. In some embodiments, d and e are integers each independently ranging from 1 to 12.

In some embodiments, the reactive group Y is a carbonyl-reactive group. Suitable carbonyl-reactive groups include hydrazine, hydrazine derivatives, and amine. In other embodiments, the reactive group Y is an amine-reactive group. Suitable amine-reactive groups include active esters, such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like. In yet embodiments, the reactive group Y is a thiol-reactive group. Suitable thiol-reactive groups include non-polymerizable Michael acceptors, haloacetyl groups (such as iodoacetyl), alkyl halides, maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent.

Specific examples of caged haptens are provided below, including caged 7-(Diethylamino) coumarin-3-carboxylic acid (DCC), caged biotin, caged nitropyrazole, caged thiazolesulfonamide (TS), and caged benzofurazan (BF). Each of the caged haptens below comprise a substrate for an alkaline phosphatase enzyme.

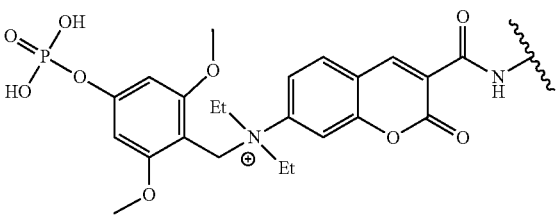

DCC

-continued
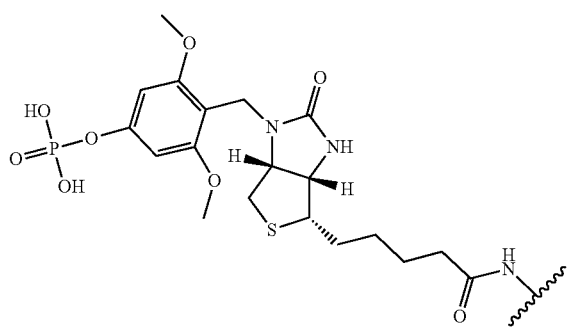
Biotin
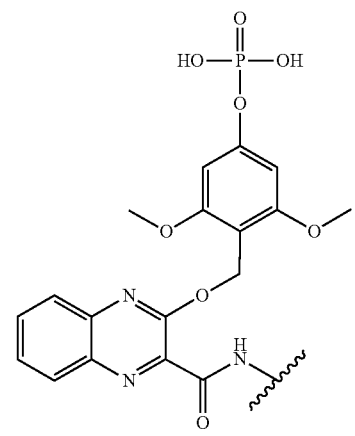
HQ
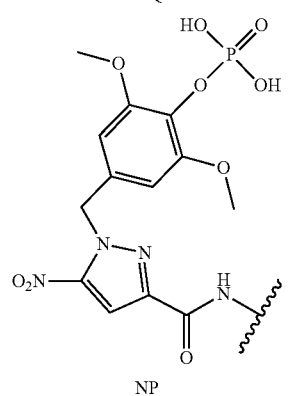
NP
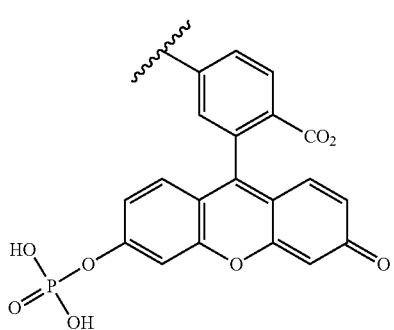
Fluorescein or FITC
-continued
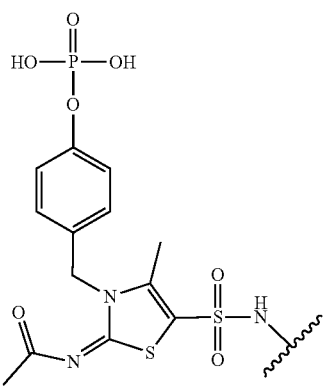
TS
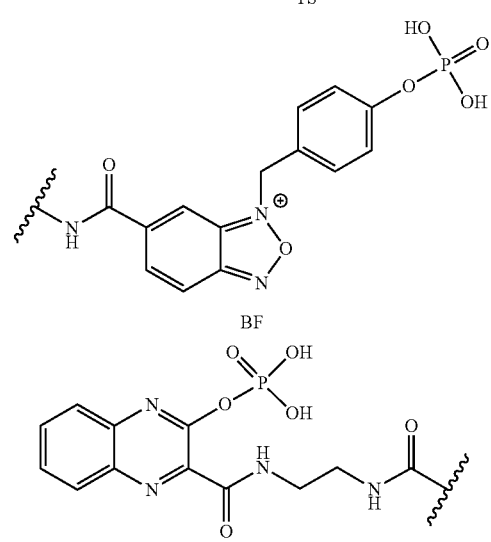
BF
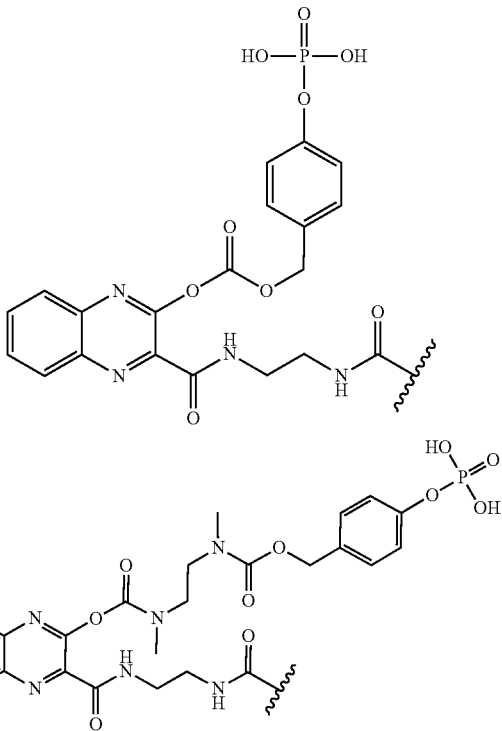

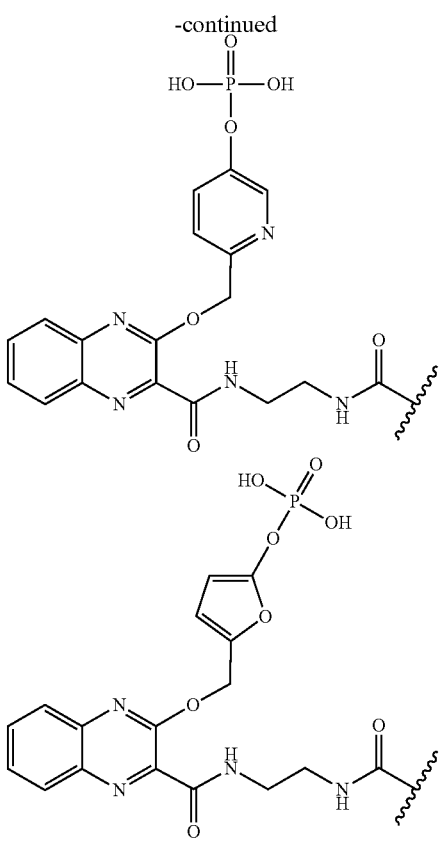

Figure 15:
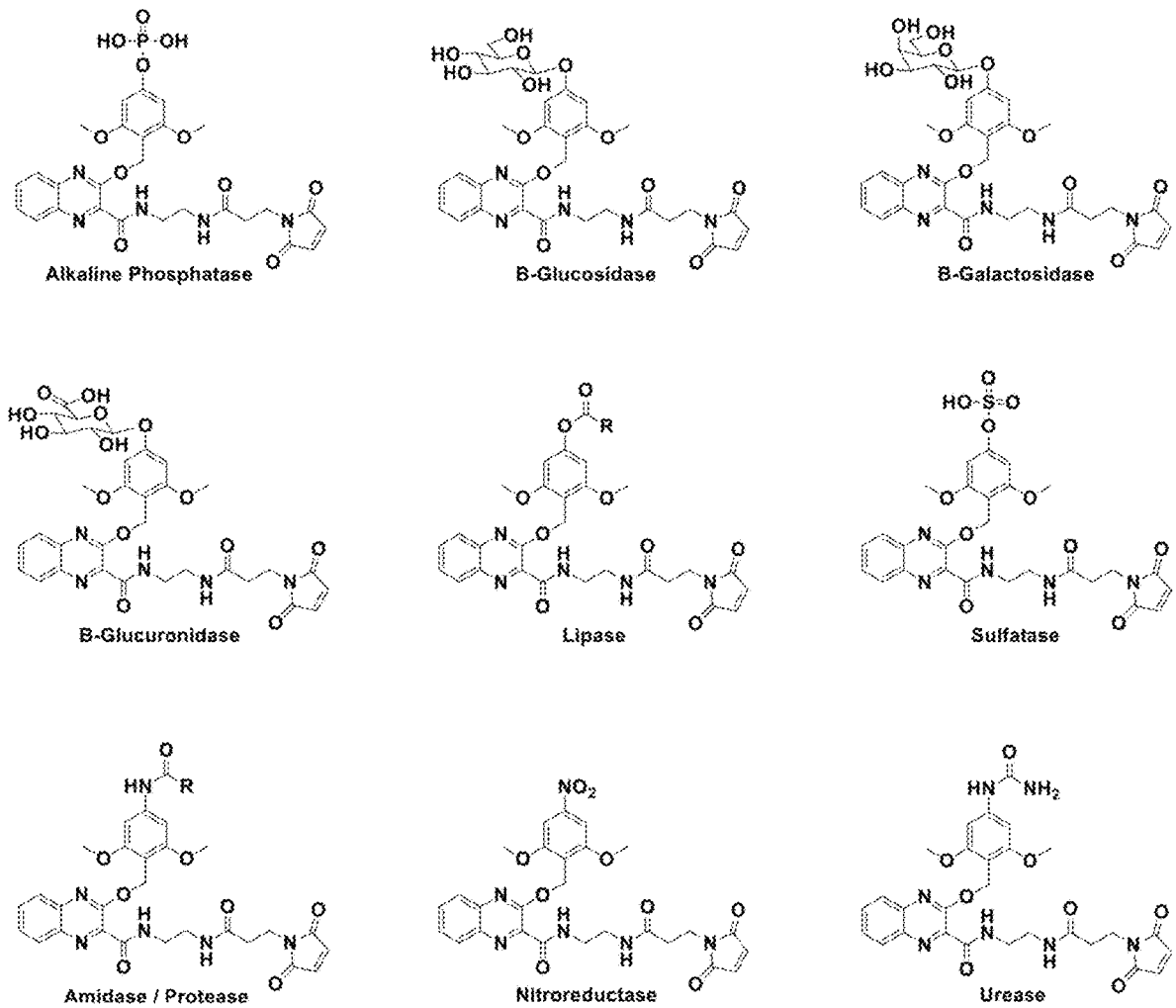
FIG. 15 illustrates the structures of caged haptens and specifies particular enzymes which may react with the enzyme substrate portion of the caged hapten.

Other examples of caged haptens, including specific enzymes that act upon the enzyme substrate portion of the caged hapten, are provided in FIG. 15.

Synthesis of Caged Haptens

The caged happens may be synthesized according to any methods known to those of ordinary skill in the art. For example, a caging group may be prepared starting with a substituted 4-hydroxybenzaldehyde. The hydroxyl group of the substituted 4-hydroxybenzaldehyde may be substituted by a phosphate group, followed by reduction of the aldehyde and substitution of the resulting benzyl alcohol with a halogen through an Appel reaction. A caging group may then be installed on the hapten of interest by reaction of the halogen-substituted caging group with the hapten under basic conditions (if the hapten contains multiple nucleophilic groups, it may require protection chemistry to select the desired position for caging). The protected phosphate group of the caging group may then be deprotected using trimethylsilyl bromide, followed by reaction of the caged hapten with a reactive group (i.e. maleimide) to facilitate conjugation with an antibody.

The synthesis of a "Caged HQ Hapten" (see FIG. 1B) illustrated in Example 1 and at Scheme 3. The synthesis of a "Caged NP Hapten" is illustrated below in Scheme 1.

Scheme 1: Synthesis of a Caged NP Hapten started with a substitued 4-hyrdoxybenzaldehyde.

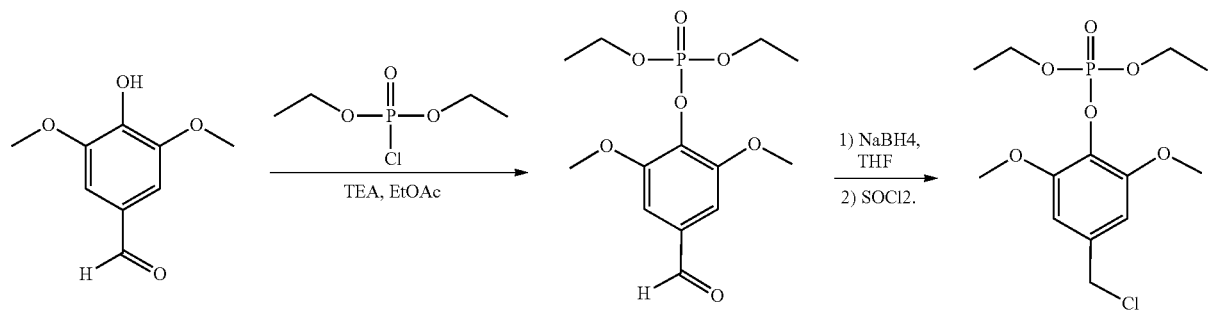

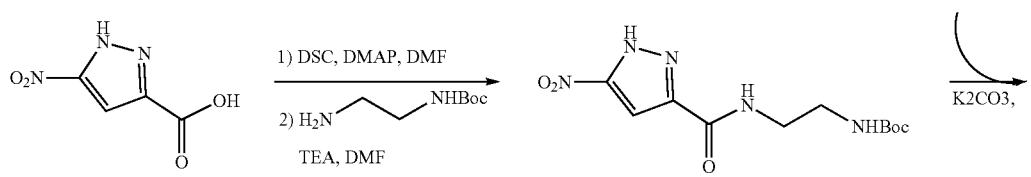

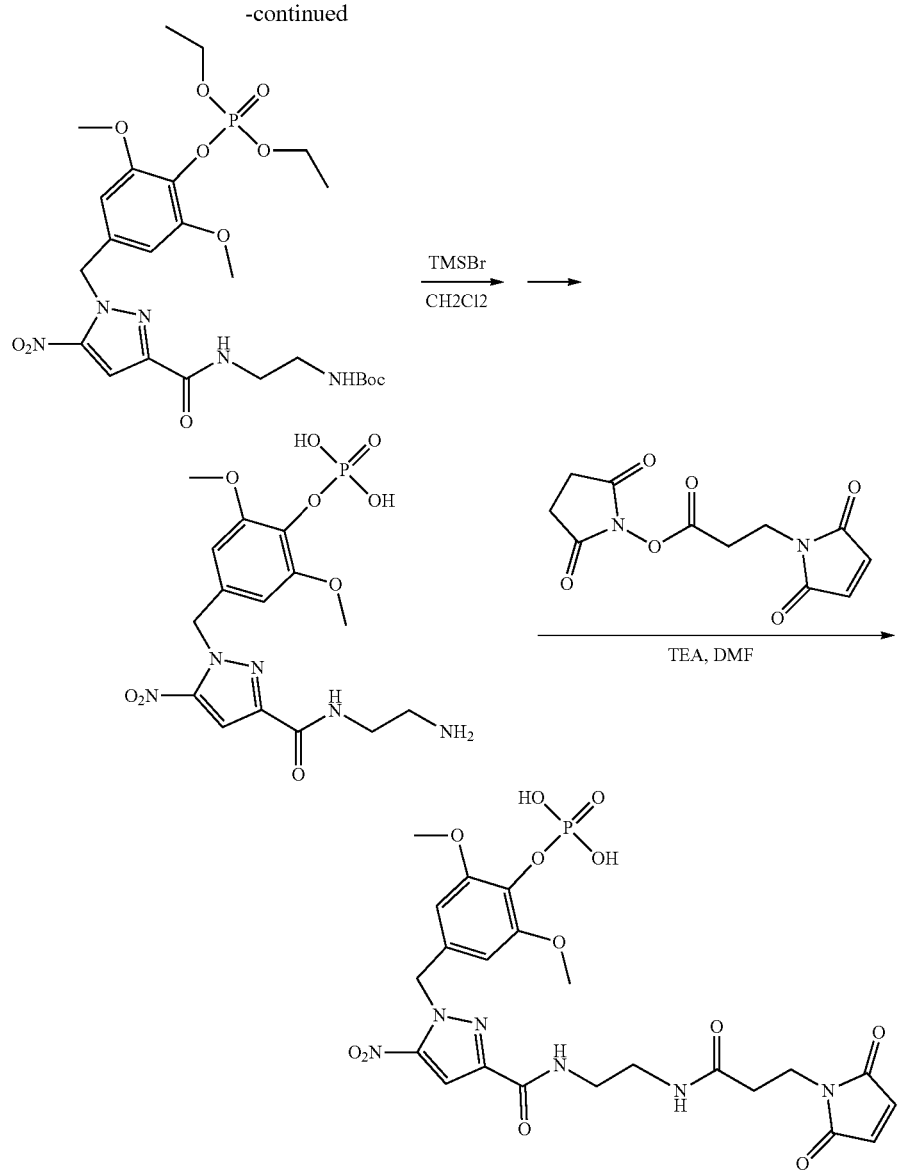

Conjugates of Caged Haptens

The present disclosure provides novel conjugates comprising a caged hapten. In some embodiments, the caged hapten is conjugated to specific binding entity, e.g. an antibody or nucleic acid probe. In other embodiments, the caged hapten is conjugated to an antibody, as in Formula (IV):

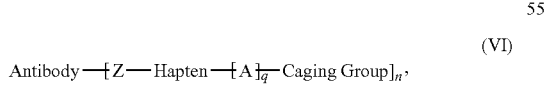
(VI)

where
A is a group comprising a branched or unbranched, substituted or unsubstituted, saturated or unsaturated aliphatic group having between 1 and 15 carbon atoms, and optionally having one or more heteroatoms selected from the group consisting of O, N, or S;
Q is 0 or 1;
n is an integer ranging from 1 to 25, and
Z is a bond, or a group comprising a branched or unbranched, substituted or unsubstituted, saturated or unsaturated aliphatic group having between 1 and 30 carbon atoms, and optionally having one or more heteroatoms selected from the group consisting of O, N, or S. In some embodiments, Z comprises a group having the structure of any of Formulas (IIIA), (IIIB), or (IIIC).

In some embodiments, n is an integer ranging from 1 to 8. In other embodiments, n is an integer ranging from 1 to 6. In yet other embodiments, n is an integer ranging from 1 to 4. In further embodiments, n is an integer ranging from 2 to 5. In yet further embodiments, n is 3. In even further embodiments, n is 4.

In some embodiments, the caged haptens are conjugated to primary antibodies (e.g. a caged hapten conjugated to an antibody specific for Beta-Catenin). In other embodiments, the caged haptens are conjugated to secondary antibodies (e.g. a caged hapten conjugated to an antibody specific for an anti-Beta-Catenin antibody).

The caged haptens may be coupled to any portion of an antibody. Three functional groups of antibodies suitable for covalent modifications include (i) amines (—NH2), (ii) thiol groups (—SH), and (iii) carbohydrate residues. As such, any of the caged haptens disclosed herein may be coupled to amine residues, thiol residues, and carbohydrate residues or any combination thereof. In some embodiments, the caged haptens are coupled to Fc portions of the antibody.

Synthesis of Caged Hapten Conjugates

The conjugates of the present disclosure may be synthesized according to any means known to those of ordinary skill in the art.

Fc portion of the antibody through a reactive functional group on the caged hapten (e.g. with a carbonyl-reactive group, such as hydrazide group).

In yet other embodiments, a caged hapten is conjugated to a lysine residue of an antibody. As illustrated in the synthetic scheme which follows (Scheme 2), in some embodiments, the antibody is first treated with an excess of Traut's reagent (2-iminothiolane hydrochloride) before adding an excess of an appropriately functionalized caged hapten (e.g. one bearing a thiol reactive group, such as a maleimide group).

Scheme 2: Synthetic methodology illustrating the reaction between an amino group on an antibody ("Ab") with Traut's Reagent, followed by coupling of the resulting intermediate with a Caged HQ Maleimide.

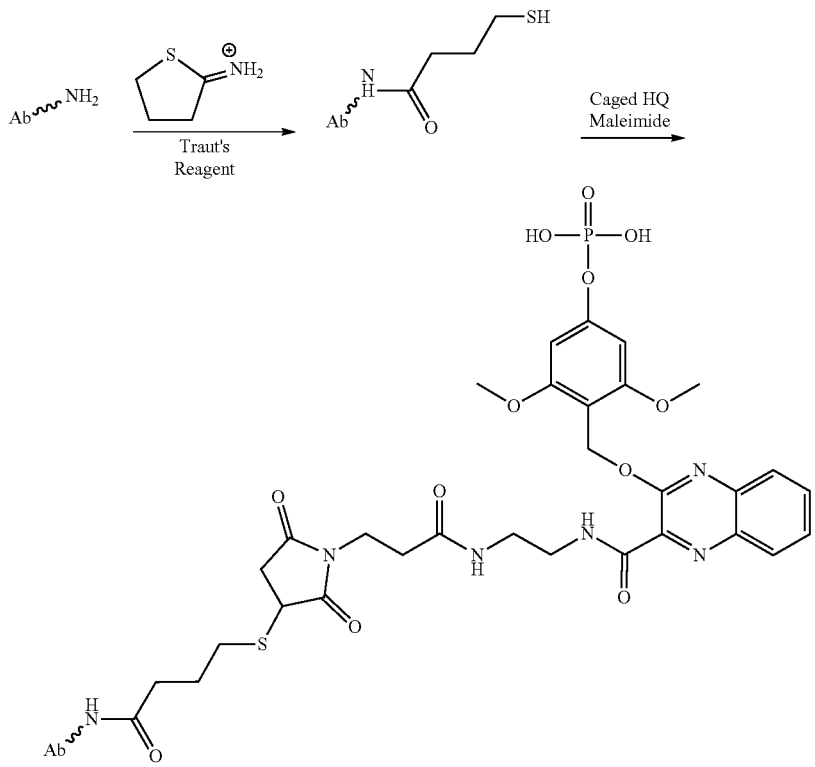

In some embodiments, a caged hapten is conjugated to a thiol group of an antibody. In some embodiments, thiol groups are first introduced to the antibody by treating the antibody with a reducing agent such as dithiothreitol (DTT) or dithioerythritol (DTE). For a mild reducing agent, such as DTE or DTT, a concentration of between about 1 mM and about 40 mM (for example, a concentration of between about 5 mM and about 30 mM or between about 15 mM and about 25 mM) is utilized to introduce a limited number of thiols (such as between about 2 and about 6) to the antibody, while keeping the antibody intact (which can be determined by size-exclusion chromatography). Following treatment with the reducing agent, an excess of a caged hapten bearing a thiol reactive group (e.g. a maleimide group) is introduced to form the respective caged hapten-antibody conjugate.

In other embodiments, a caged hapten is conjugated to a Fc portion of an antibody. In some embodiments, an Fc portion of an antibody is first oxidized to form an aldehyde and the caged hapten is subsequently coupled to the oxidized Following synthesis, the conjugates may be purified, such as by size exclusion chromatography (SEC), and then characterized, such as by gel electrophoresis and/or UV-Vis.

Detection of Caged Hapten Antibody Conjugates

In some embodiments, detection reagents are utilized to enable detection of caged hapten conjugates, or complex of a caged hapten conjugate and a target. In some embodiments, the detection reagents employed are specific to the respective unmasked hapten corresponding to the caged hapten of any caged hapten-conjugate. Thus, the terms "respective unmasked hapten" or "unmasked hapten" refer to caged haptens that have been "un-caged" with an appropriate unmasking enzyme to reveal the "native" hapten, i.e. an unmasking enzyme that is reactive with an enzyme substrate portion of the caged hapten. The steps of "uncaging" or "unmasking" are described further herein and depicted at least in FIG. 2. As will be described herein, detection reagents may also include components designed to increase signal, e.g. signal amplification components or signal amplification kits.

In some embodiments, the detection reagents specific to the unmasked hapten are secondary antibodies specific to the unmasked hapten of the caged hapten conjugate, i.e. anti-unmasked hapten antibodies, and are themselves conjugated to a detectable moiety. A "detectable moiety" is a molecule or material that can produce a detectable (such as visually, electronically or otherwise) signal that indicates the presence (i.e. qualitative analysis) and/or concentration (i.e. quantitative analysis) of the caged hapten-antibody conjugate and/or unmasking enzyme-antibody conjugate in a sample. A detectable signal can be generated by any known or yet to be discovered mechanism including absorption, emission and/or scattering of a photon (including radio frequency, microwave frequency, infrared frequency, visible frequency and ultra-violet frequency photons).

In some embodiments, the detectable moiety of the anti-unmasked hapten antibody includes chromogenic, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Of course, the detectable moieties can themselves also be detected indirectly, e.g. if the detectable moiety is a hapten, then yet another antibody specific to that detectable moiety may be utilized in the detection of the detectable moiety, as known to those of ordinary skill in the art.

In some embodiments, the anti-unmasked hapten antibody includes a detectable moiety selected from the group consisting of Cascade Blue acetyl azide; Dapoxylsulfonic acid/carboxylic acid DY-405; Alexa Fluor 405 Cascade Yellow pyridyloxazole succinimidyl ester (PyMPO); Pacific Blue DY-415; 7-hydroxycoumarin-3-carboxylic acid DYQ-425; 6-FAM phosphoramidite; Lucifer Yellow; Alexa Fluor 430 Dabcyl NBD chloride/fluoride; QSY 35 DY-485XL; Cy2 DY-490; Oregon Green 488 Alexa Fluor 488 BODIPY 493/503 $C_3$ DY-480XL; BODIPY FL $C_3$ BODIPY FL $C_5$ BODIPY FL-X DYQ-505; Oregon Green 514 DY-510XL; DY-481XL; 6-carboxy-4',5'-dichloro-2', 7'-dimethoxyfluorescein succinimidyl ester (JOE); DY-520XL; DY-521XL; BODIPY R6G C3 erythrosin isothiocyanate; 5-carboxy-2', 4',5', 7'-tetrabromosulfonefluorescein Alexa Fluor 532 6-carboxy-2',4,4',5'7,7'-hexachlorofluorescein succinimidyl ester (HEX); BODIPY 530/550 C3 DY-530; BODIPY TMR-X DY-555; DYQ-1; DY-556; Cy3 DY-547; DY-549; DY-550; Alexa Fluor 555 Alexa Fluor 546 DY-548; BODIPY 558/568 C3 Rhodamine red-X QSY 7 BODIPY 564/570 C3 BODIPY 576/589 C3 carboxy-X-rhodamine (ROX); Alexa Fluor 568 DY-590; BODIPY 581/591 C3 DY-591; BODIPY TR-X Alexa Fluor 594 DY-594; carboxynaphthofluorescein DY-605; DY-610; Alexa Fluor 610 DY-615; BODIPY 630/650-X erioglaucine; Alexa Fluor 633 Alexa Fluor 635 succinimidyl ester; DY-634; DY-630; DY-631; DY-632; DY-633; DYQ-2; DY-636; BODIPY 650/665-X DY-635; Cy5 Alexa Fluor 647 DY-647; DY-648; DY-650; DY-654; DY-652; DY-649; DY-651; DYQ-660; DYQ-661; Alexa Fluor 660 Cy5.5 DY-677; DY-675; DY-676; DY-678; Alexa Fluor 680 DY-679; DY-680; DY-682; DY-681; DYQ-3; DYQ-700; Alexa Fluor 700 DY-703; DY-701; DY-704; DY-700; DY-730; DY-731; DY-732; DY-734; DY-750; Cy7 DY-749; DYQ-4; and Cy7.5.

Fluorophores belong to several common chemical classes including coumarins, fluoresceins (or fluorescein derivatives and analogs), rhodamines, resorufins, luminophores and cyanines. Additional examples of fluorescent molecules can be found in Molecular Probes Handbook-A Guide to Fluorescent Probes and Labeling Technologies, Molecular Probes, Eugene, OR, ThermoFisher Scientific, 11$^{th}$ Edition. In other embodiments, the fluorophore is selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In other embodiments, the fluorescent moiety is selected from a CF dye (available from Biotium), DRAQ and CyTRAK probes (available from BioStatus), BODIPY (available from Invitrogen), Alexa Fluor (available from Invitrogen), DyLight Fluor (e.g. DyLight 649) (available from Thermo Scientific, Pierce), Atto and Tracy (available from Sigma Aldrich), FluoProbes (available from Interchim), Abberior Dyes (available from Abberior), DY and MegaStokes Dyes (available from Dyomics), Sulfo Cy dyes (available from Cyandye), HiLyte Fluor (available from AnaSpec), Seta, SeTau and Square Dyes (available from SETA BioMedicals), Quasar and Cal Fluor dyes (available from Biosearch Technologies), SureLight Dyes (available from APC, RPEPerCP, Phycobilisomes) (Columbia Biosciences), and APC, APCXL, RPE, BPE (available from Phyco-Biotech, Greensea, Prozyme, Flogen).

In other embodiments, the anti-unmasked hapten antibody is conjugated to an enzyme. In these embodiments, the final proximity signal can be generated with any enzyme conjugated to the relevant anti-unmasked hapten antibody, with the exception of the enzyme that is used for unmasking (e.g. an unmasking enzyme of an unmasking enzyme-antibody conjugate, described further herein). In some embodiments, suitable enzymes include, but are not limited to, horseradish peroxidase, alkaline phosphatase, acid phosphatase, glucose oxidase, neuramindase, β-galactosidase, β-glucuronidase or β-lactamase. In other embodiments, enzymes include oxidoreductases or peroxidases (e.g. HRP). In these embodiments, the enzyme conjugated to the anti-unmasked hapten antibody catalyzes conversion of a chromogenic substrate, a covalent hapten, a covalent fluorophore, non-covalent chromogens, and non-covalent fluorophores to a reactive moiety which labels a sample proximal to or directly on the target.

Particular non-limiting examples of chromogenic compounds/substrates include diaminobenzidine (DAB), 4-nitrophenylphospate (pNPP), fast red, bromochloroindolyl phosphate (BCIP), nitro blue tetrazolium (NBT), BCIP/NBT, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazole (AEC), fuchsin, iodonitrotetrazolium (INT), tetrazolium blue, and tetrazolium violet. DAB, which is oxidized in the presence of peroxidase and hydrogen peroxide, results in the deposition of a brown, alcohol-insoluble precipitate at the site of enzymatic activity.

In some embodiments, the chromogenic substrates are signaling conjugates which comprise a latent reactive moiety and a chromogenic moiety. In some embodiments, the latent reactive moiety of the signaling conjugate is configured to undergo catalytic activation to form a reactive species that can covalently bond with the sample or to other detection components. The catalytic activation is driven by one or more enzymes (e.g., oxidoreductase enzymes and peroxidase enzymes, like horseradish peroxidase) and results in the formation of a reactive species. These reactive species are capable of reacting with the chromogenic moiety proximal to their generation, i.e. near the enzyme. Specific examples of signaling conjugates are disclosed in US Patent Publication No. 2013/0260379, the disclosure of which is hereby incorporated by reference herein in its entirety.

Other substrates include those set forth in U.S. Pat. No. 5,583,001, U.S. application publication No. 2012/0171668, and PCT/EP2015/0533556, the disclosures of which are hereby incorporate by reference herein in their entireties. Suitable chromogenic substrates or fluorescent substrates coupled to TSA or QM conjugates, as noted in the above incorporated references, include N,N'-biscarboxypentyl-5, 5'-disulfonato-indo-dicarbocyanine (Cy5), 4-(dimethyl-amino) azobenzene-4'-sulfonamide (Dabsyl), tetramethyl-rhodamine (Tamra), and Rhodamine 110 (Rhodamine).

In some embodiments, the chromogenic substrates, fluorescent substrates, or signaling conjugates are selected such that peak detectable wavelengths of any chromogenic moiety do not overlap with each other and are readily detectable by a pathologist or an optical detector (e.g. a scanner). In some embodiments, the chromogenic moieties are selected such that the peak wavelengths of the different chromogenic moieties are separated by at least about 50 nm. In other embodiments, the chromogenic moieties are selected such that the peak wavelengths of the different chromogenic moieties are separated by at least about 70 nm. In yet other embodiments, the chromogenic moieties are selected such that the peak wavelengths of the different chromogenic moieties are separated by at least about 100 nm.

In yet further embodiments, the chromogenic moieties are selected such that the chromogenic moieties, when introduced to the tissue specimen, provide for different colors (e.g. yellow, blue, magenta). In some embodiments, the chromogenic moieties are selected such that they provide a good contrast between each other, e.g. a separation of colors that are optically recognizable. In some embodiments, the chromogenic moieties are selected such that when placed in close proximity of each other provide for a signal or color that is different than the signals or colors of either of the chromogenic moieties when observed alone.

Proximity Detection Using Caged Hapten Conjugates

As will be described in more detail herein, the present disclosure enables the detection of protein dimers or proteins in close proximity to each other. Non-limiting examples of protein-protein interactions include any of the Her1/2/3/4 proteins with each other; PD-1 with PD-L1; and/or PD-L2, EGFR (Her1) with any of it associated ligands (AREG, EREG).

Without wishing to be bound by any particular theory, it is believed that the disclosed proximity assay is more general than merely measuring protein-protein interactions. Indeed, the disclosed assay allows for the measurement of the proximity of binding moieties. In practice, the binding moieties (e.g. antibodies) may be directed against targets with minimal or no distance between them. Examples of this could include signaling events like phosphorylation of proteins. In this case, if one antibody is directed against an epitope on a protein (e.g. HER2), and a second antibody is directed against all phospho-tyrosines, then the proximity signal would represent all the phosphorylated HER2 proteins. This type of assay is more binary (yes/no) than pairs of proteins that interact with each other.

In some embodiments, the assay is able to detect protein dimers or proteins having a proximity of 5000 nm or less. In other embodiments, the assay is able to detect protein dimers or proteins having a proximity of 2500 nm or less. In yet other embodiments, the assay is able to detect protein dimers or proteins having a proximity of 1000 nm or less. In further embodiments, the assay is able to detect protein dimers or proteins having a proximity of 500 nm or less.

The skilled artisan will appreciate that the caged hapten conjugates may be used in both simplex assays (detection of protein dimers or protein proximity) and multiplex assays (detection of protein dimers or protein proximity and detection of total protein). "Total protein" refers to the normal IHC visualization of any given protein, whereas a proximity signal is the portion of this protein that is involved in a given interaction. For example, and in the case of a PD-1/PD-L1 assay, the proximity signal would visualize only the interaction between PD-1 and PD-L1, whereas the total protein signal would visualize all PD-1 in the sample. Expressing the score for proximity as a numerator and the score for total protein as a denominator could give the fraction or percentage of PD-1 that is involved in an interaction. This may be important as a diagnostic for detecting active pharmaceutical ingredients that disturb protein-protein interaction where the expression of protein is less important that the number of interacting proteins. This is believed to hold true for phosphorylation, as described above, where instead of just receiving an arbitrary score for the phosphorylated signal, one may be able to quantify what percentage of a give protein is phosphorylated.

Figure 4:
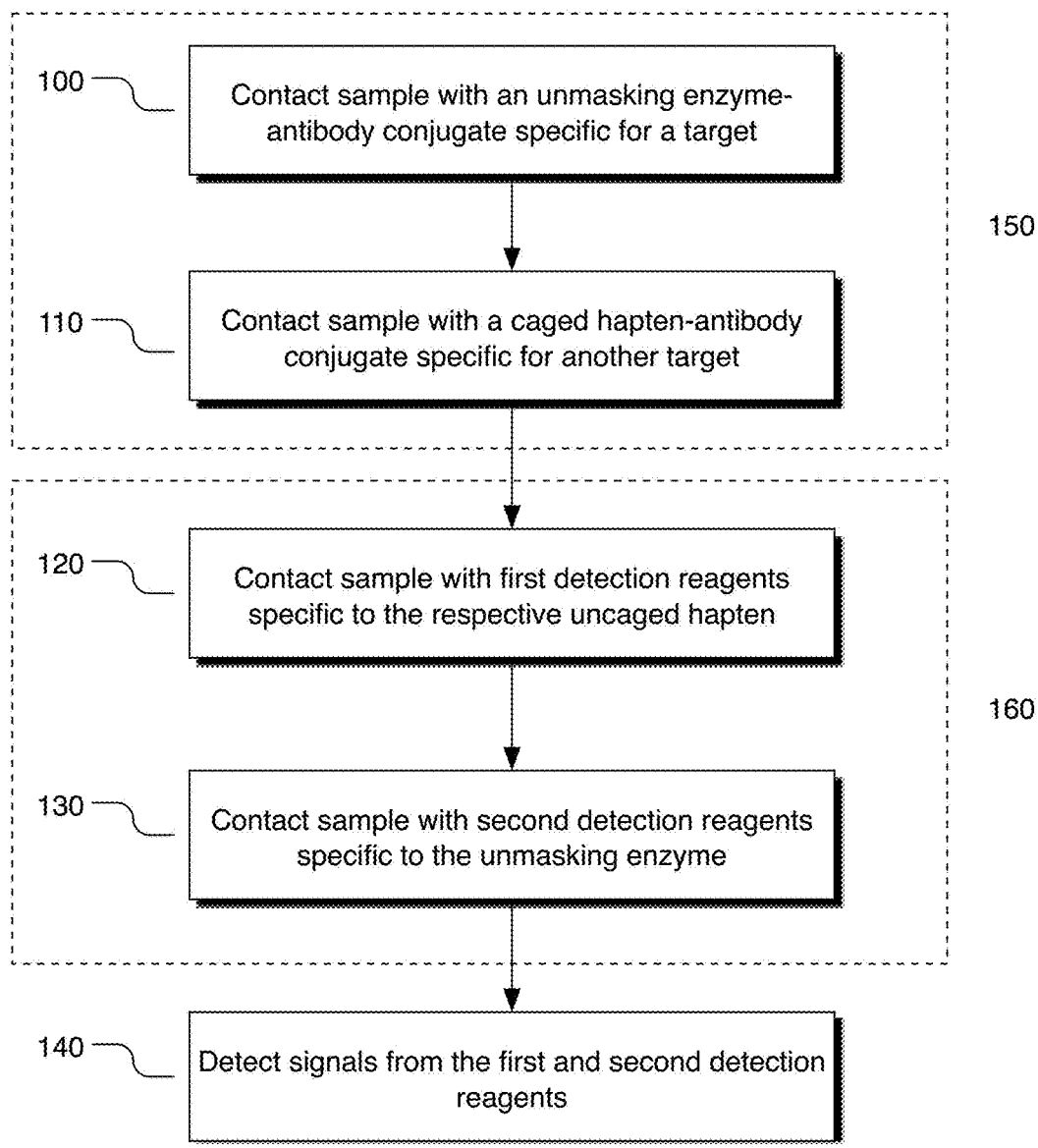
FIG. 4 provides a flowchart illustrating the steps of detecting protein dimers and/or total protein in a sample.

With reference to FIG. 4, the detection of protein dimers takes place in two general stages. In a first stage, a sample is labeled with an antibody conjugates at step 150. In a second stage, the sample is contacted with first detection reagents, and optionally second detection reagents, at step 160.

In some embodiments, a sample is first contacted at step 100 with an unmasking enzyme-antibody conjugate specific for a target, to form a target-unmasking enzyme-antibody conjugate complex. Subsequently, the sample is then contacted at step 110 with a caged hapten-antibody conjugate, such as those of Formula (III), and specific for another target, to form a target-caged hapten-antibody conjugate complex. As will be appreciated by the skilled artisan, an unmasking enzyme is selected that is reactive with an enzyme substrate portion of the caged hapten-antibody conjugate. The skilled artisan will also appreciate that steps 100 and 110 may be performed in any order or may be performed simultaneously. In some embodiments, a reversible enzyme inhibitor is also introduced prior to or simultaneously with the introduction of the caged hapten-antibody conjugate. For example, in some embodiments, the caged hapten-antibody conjugate may be formulated with a phosphate buffer.

As noted herein, the caged hapten portion of the caged hapten-antibody conjugate is capable of becoming unmasked to provide the respective unmasked hapten, i.e. the native hapten. As illustrated in FIG. 2, if a first target 101 is in sufficient proximity to a second target 102, the caged hapten-antibody conjugate 103A will be provided in proximity (the proximity being labeled 105) to the unmasking enzyme-antibody conjugate 104 such that the unmasking enzyme of the unmasking enzyme-antibody conjugate 104 may react with the enzyme substrate of the caged hapten-antibody conjugate 103A. This in turn results in the formation of a first target unmasked hapten-antibody conjugate complex (103B). As illustrated in FIG. 2, the first target unmasked hapten-antibody conjugate complex (103B) is able to bind or be recognized by other specific binding entities (e.g. a secondary antibody 106).

In some embodiments, the method also includes one or more "decaging steps" where on-slide conditions are changed to enhance enzyme activity. During the antibody conjugate binding portion of the assay, when the conjugates are in excess, steps are taken to prevent incidental "decaging" of the caged hapten which would lead to false positive results. These steps include adding reversible enzyme inhibitors (e.g. to prevent the action of the enzyme on the caging group). For example, in the context of alkaline phosphatase (AP), these inhibitors can include phosphate, phenylalanine and EDTA which are believed to be able to reduce the enzyme activity by different mechanisms. In some embodiments, non-bound antibody conjugates are removed by washing, it is then necessary to change the on-slide conditions to be favorable for the optimal enzyme activity to allow "decaging" to occur. Each decaging enzyme will have its own optimal conditions (buffers, salts, cofactors, temperature). These "decaging steps" including any of washing steps, steps to change the pH of the solutions or reagents present on the slide, the addition of cofactors, or the changing of temperature (e.g. temperatures ranging from about 37° C. to about 50° C.) are chosen to enhance the activity of the enzyme and promote "decaging," without interfering with the specific binding of the antibody conjugates. For example, and in the case of AP, washes are used to remove residual inhibitors (e.g. phosphate), buffers are also used to increase the activity (e.g. Tris, to adjust the pH to greater than about 8), and cofactors (e.g. magnesium) are added. In some embodiments, each of these conditions are optimized in the context of the entire assay, for example the activity of AP is enhanced by the addition of magnesium ions ranging in concentration from 1 mM to 1 M. However at concentrations of magnesium ions greater than 100 mM the antibody binding is affected, so this limits the amount that may be added. Another example of an optimizable step is the temperature of the "decaging" steps. The "decaging" event after the enzymatic step is driven by thermodynamics and can be accelerated by heating. However, temperatures greater than 60° C. can negatively affect both the enzyme activity and the antibody conjugate binding.

Figure 3:
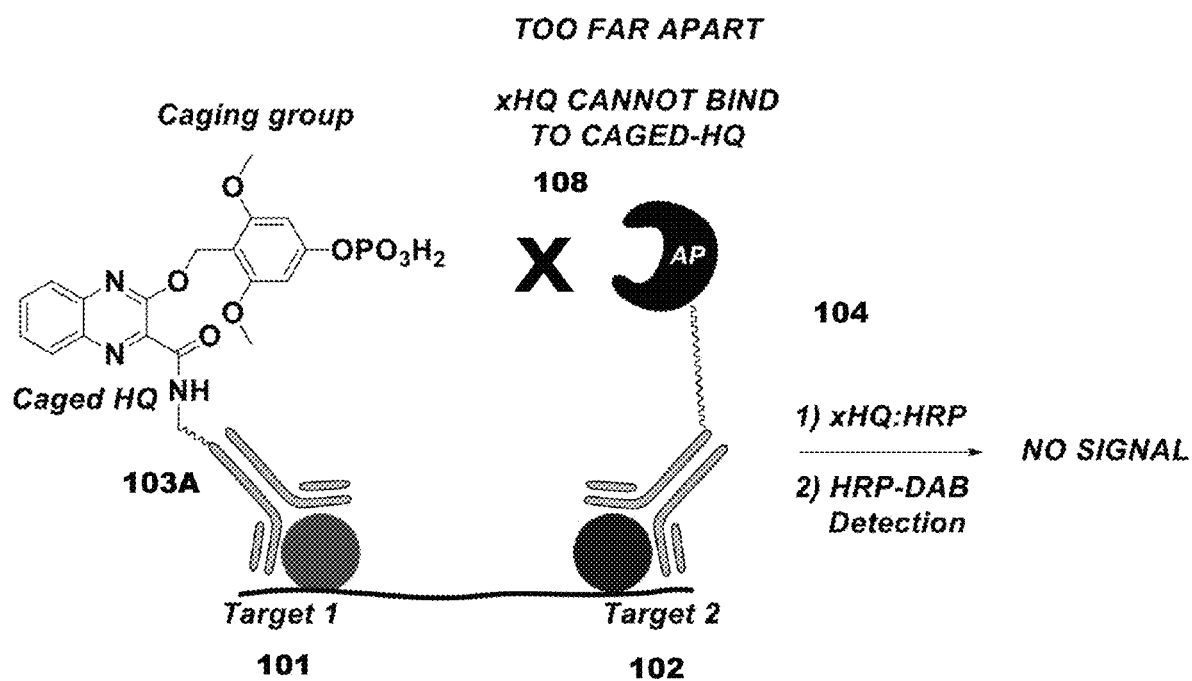
FIG. 3 is a schematic illustrating an unmasking enzyme-antibody conjugate (bound to Target 2) and a caged hapten-antibody conjugate (bound to Target 1) where the two targets are not in close proximity to each other, such that the unmasking enzyme of the unmasking enzyme-antibody conjugate does not interact with an enzyme substrate portion of the caged hapten-antibody conjugated, and thus the caged hapten remains masked and unable to be detected.

On the other hand, and as illustrated in FIG. 3, if a first target 101 is not in sufficient proximity to a second target 102, the caged hapten-antibody conjugate 103A will not be provided in proximity (the proximity being labeled 108) to the unmasking enzyme-antibody conjugate 104. In this instance, the unmasking enzyme will not be reactive with the enzyme substrate of the caged hapten-antibody conjugate 103A, and thus the caged hapten will remain in a masked or protected state, i.e. it is not capable of binding or being recognized by other specific binding entities.

Figure 12:
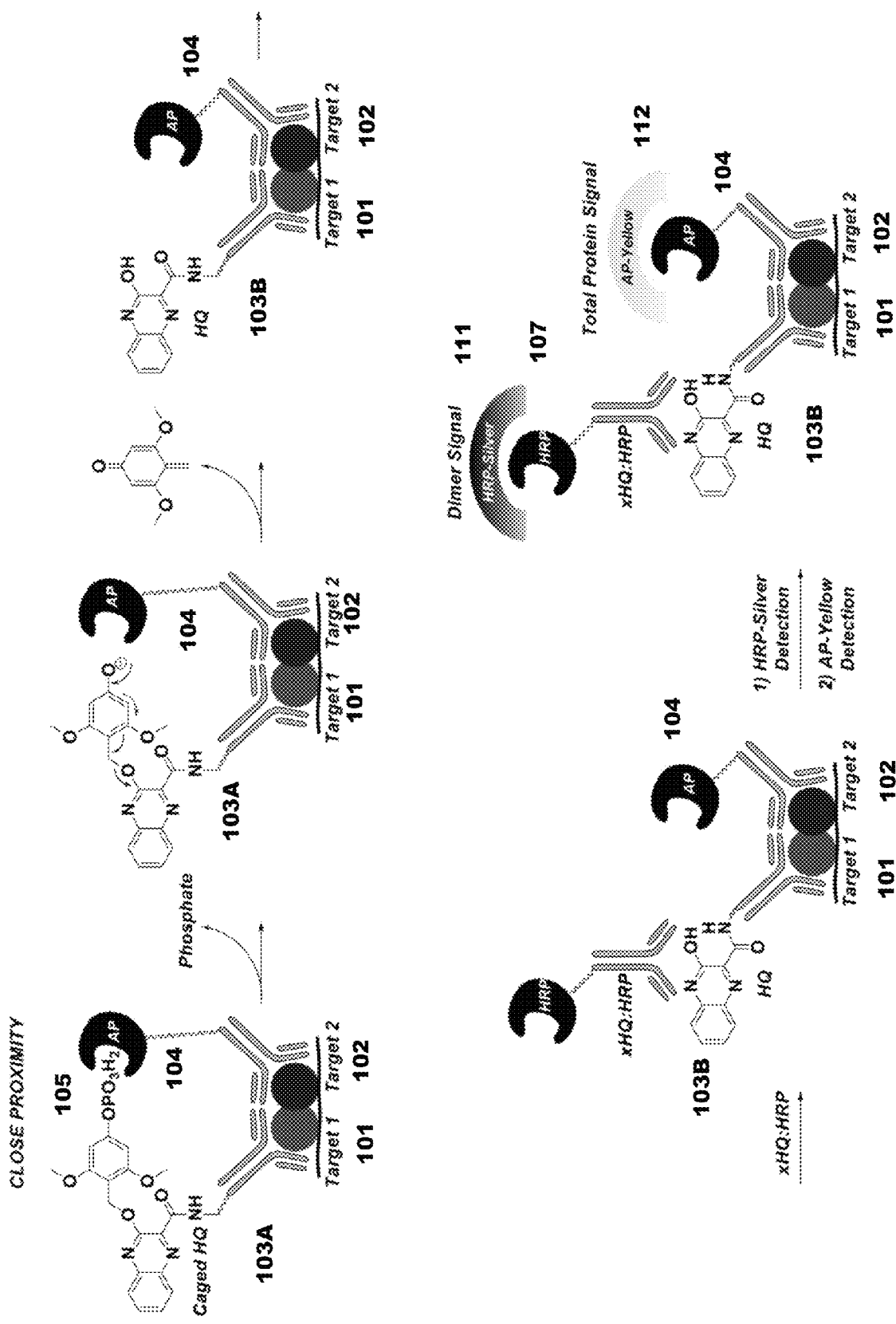
FIG. 12 is a schematic illustrating multiplex detection of both proteins (Target 1 and Target 2) in close proximity and total protein (Target 2).

Referring to FIGS. 2, 4, and 12, in some embodiments, the sample is then contacted at step 120 with first detection reagents (106), the first detection reagents being specific to the unmasked hapten of the first target unmasked hapten-antibody conjugate complex (103B). In some embodiments, the first detection reagents include a secondary antibody (106) specific for the unmasked hapten (103B), namely an anti-unmasked hapten antibody. In some embodiments, the anti-unmasked hapten antibody (106) is conjugated to a detectable moiety (e.g. in FIGS. 2 and 12, the detectable moiety is a HRP enzyme, where the HRP enzyme acts upon a substrate, such as a silver chromogenic substrate (111)). The skilled artisan will, of course, appreciate that the first detection reagents (106) will only bind if the native or unmasked hapten (103B) of the first target unmasked hapten-antibody conjugate complex is revealed by the unmasking enzyme of the unmasking enzyme-antibody conjugate (104). Thus, signal (107) from the detectable moiety of the first detection reagents (106) will only be able to be detected at step 140 if the first and second targets (101 and 102), and, hence, the antibody conjugates (103A and 104), are in close proximity to each other. Here, detected signal (107) is representative of a protein dimer or proteins/targets in close proximity.

In some embodiments, an amplification step may be carried out to increase detectable signal. For example, amplification components may be introduced to further label the unmasked hapten of the first target unmasked hapten-antibody conjugate with additional reporter moieties, e.g. additional haptens or other "detectable moieties." By way of example, an anti-unmasked hapten antibody conjugated to an amplification hapten (or, in other embodiments, conjugated to an enzyme) may be introduced to label the unmasked hapten of the first target unmasked hapten-antibody conjugate with a plurality of amplification haptens. Subsequently, anti-amplification hapten antibodies, each conjugated to a detectable moiety, may be introduced. In some embodiments, the anti-amplification hapten antibodies are conjugated to an enzyme, where the enzyme acts upon an introduced substrate to produce a signal (e.g. a chromogenic substrate or a fluorescent substrate to produce a visual signal). TSA and QM conjugates, each described herein, may be used in any amplification step. In some examples, signal amplification is carried out using OPTIV-IEW Amplification Kit (Ventana Medical Systems, Inc., Tucson, Ariz., Catalog No. 760-099).

The skilled artisan will appreciate that the unmasking enzyme of the unmasking enzyme-antibody conjugate may serve two functions, namely (i) to unmask or reveal a caged hapten; and (ii) to react with another substrate (e.g. a chromogenic substrate or a fluorescent substrate) such that a signal independent from that generated by the unmasked hapten (i.e. the unmasked hapten-antibody conjugate complex) may be detected. Accordingly, the presently disclosed system allows for the proximity between two proteins to be visualized within the context of the total protein stain for one of the proteins. Without wishing to be bound by any particular theory, it is believed that the ability to multiplex proximity detection within the context of another protein stain is a feature that allows for the possibility of having a speedy, guided slide read (i.e. only looking for proximity signal within the total protein) or the ability to quantitate the percentage of protein that is interacting with another (a method of scoring the proximity assay).

Referring again to FIGS. 2, 4, and 12, following the introduction of the first detection reagents (106), second detection reagents including a second detectable moiety (109) may optionally be introduced to the sample at step 130 such that total protein may be detected. In some embodiments, the second detectable moiety provides signals (112) different from that of the first detectable moiety (107). In some embodiments, the second detectable moiety comprises a substrate for the unmasking enzyme, e.g. a chromogenic substrate that provides yellow signals (109). In other embodiments, the second detectable moiety comprises a signaling conjugate. The skilled artisan will also appreciate that steps 120 and 130 may be performed in any order or may be performed simultaneously.

In some embodiments, the biological samples are pretreated with an enzyme inactivation composition to substantially or completely inactivate endogenous peroxidase activity. For example, some cells or tissues contain endogenous peroxidase. Using an HRP conjugated antibody may result in high, non-specific background staining. This non-specific background can be reduced by pre-treatment of the sample with an enzyme inactivation composition as disclosed herein. In some embodiments, the samples are pre-treated with hydrogen peroxide only (about 1% to about 3% by weight of an appropriate pre-treatment solution) to reduce endogenous peroxidase activity. Once the endogenous peroxidase activity has been reduced or inactivated, detection kits may be added, followed by inactivation of the enzymes present in the detection kits, as provided above. The disclosed enzyme inactivation composition and methods can also be used as a method to inactivate endogenous enzyme peroxidase activity.

In some embodiments if the specimen is a sample embedded in paraffin, the sample can be deparaffinized using appropriate deparaffinizing fluid(s). After a waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

Automation

The assays and methods of the present disclosure may be automated and may be combined with a specimen processing apparatus. The specimen processing apparatus can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published patents application Ser. Nos. 20/030,211630 and 20040052685, each of which is incorporated herein by reference in its entirety. Alternatively, specimens can be manually processed.

The specimen processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized with the specimen processing apparatus using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label. Labels can include radioactive isotopes, enzyme substrates, co-factors, ligands, chemiluminescent or fluorescent agents, haptens, and enzymes.

After the specimens are processed, a user can transport specimen-bearing slides to the imaging apparatus. The imaging apparatus used here is a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application Publication No. 2014/0178169, filed on Feb. 3, 2014, entitled IMAGING SYSTEMS, CASSETTES, AND METHODS OF USING THE SAME. International Patent Application No. PCT/US2010/002772 and U.S. Patent Application Publication No. 2014/0178169 are incorporated by reference in their entities. In other embodiments, the imaging apparatus includes a digital camera coupled to a microscope.

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red. DAPI (4',6-diamidino-2-phenylindole) is a fluorescent stain that may be used.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

Detection and/or Imaging

Certain aspects, or all, of the disclosed embodiments can be automated, and facilitated by computer analysis and/or image analysis system. In some applications, precise color or fluorescence ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color or fluorescence can be measured in several different ways. For example, color can be measured as red, blue, and green values; hue, saturation, and intensity values; and/or by measuring a specific wavelength or range of wavelengths using a spectral imaging camera. The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

Kits

In some embodiments, the caged hapten conjugates of the present disclosure may be utilized as part of a "detection kit." In general, any detection kit may include one or more caged hapten conjugates and detection reagents for detecting the one or more caged hapten conjugates.

The detection kits may include a first composition comprising a caged hapten conjugate and a second composition comprising detection reagents specific to the first composition, such that the caged hapten conjugate may be detected via the detection kit. In some embodiments, the detection kit includes a plurality of caged hapten conjugates (such as mixed together in a buffer), where the detection kit also includes detection reagents specific for each of the plurality of caged hapten conjugates.

Of course, any kit may include other agents, including buffers; counterstaining agents; enzyme inactivation compositions; deparafinization solutions, etc. as needed for manual or automated target detection. The kit may also include instructions for using any of the components of the kit, including methods of applying the kit components to a tissue sample to effect detection of one or more targets therein.

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example, a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t (18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t (18q11.2) in the SYT gene region, exhibit two fusions (generated by the two labels in close proximity) signals, reflecting the two intact copies of SYT. Abnormal cells with a t (18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16 (INK4A), p14 (ARF), D9S1748, p15 (INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC-000013, nucleotides 47775912-47954023), p53 (17p13.1; e.g., GENBANK™ Accession No. NC-000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC-000012, complement, nucleotides 56196638-56200567), FUS (16p11.2; e.g., GENBANK™ Accession No. NC-000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF1, AP1 (1p32-p31; e.g., GENBANK™ Accession No. NC-000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC-000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC-000022, nucleotides 27994271-28026505); FLI1 (11q24.1-q24.3; e.g., GENBANK™ Accession No. NC-000011, nucleotides 128069199-128187521), PAX3 (2q35-q37; e.g., GENBANK™ Accession No. NC-000002, complement, nucleotides 222772851-222871944), PAX7 (1p36.2-p36.12; e.g., GENBANK™ Accession No. NC-000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC-000019, complement, nucleotides 45431556-45483036), MYCL1 (1p34.2; e.g., GENBANK™ Accession No. NC-000001, complement, nucleotides 40133685-40140274), REL (2p13-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum, Entamoeba histolytica*, and *Giardia lamblia*, as well as *Toxoplasma, Eimeria, Theileria,* and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC-001460), human adenovirus B (NC-004001), human adenovirus C(NC-001405), human adenovirus D (NC-002067), human adenovirus E (NC-003266), human adenovirus F(NC-001454), human astrovirus (NC-001943), human BK polyomavirus (V01109; GI: 60851) human bocavirus (NC-007455), human coronavirus 229E (NC-002645), human coronavirus HKU1 (NC-006577), human coronavirus NL63 (NC-005831), human coronavirus OC43 (NC-005147), human enterovirus A (NC-001612), human enterovirus B (NC-001472), human enterovirus C(NC-001428), human enterovirus D (NC-001430), human erythrovirus V9 (NC-004295), human foamy virus (NC-001736), human herpesvirus 1 (Herpes simplex virus type 1) (NC-001806), human herpesvirus 2 (Herpes simplex virus type 2) (NC-001798), human herpesvirus 3 (Varicella zoster virus) (NC-001348), human herpesvirus 4 type 1 (Epstein-Barr virus type 1) (NC-007605), human herpesvirus 4 type 2 (Epstein-Barr virus type 2) (NC-009334), human herpesvirus 5 strain AD 169 (NC-001347), human herpesvirus 5 strain Merlin Strain (NC-006273), human herpesvirus 6A (NC-001664), human herpesvirus 6B (NC-000898), human herpesvirus 7 (NC-001716), human herpesvirus 8 type M (NC-003409), human herpesvirus 8 type P (NC-009333), human immunodeficiency virus 1 (NC-001802), human immunodeficiency virus 2 (NC-001722), human metapneumovirus (NC-004148), human papillomavirus-1 (NC-001356), human papillomavirus-18 (NC-001357), human papillomavirus-2 (NC-001352), human papillomavirus-54 (NC-001676), human papillomavirus-61 (NC-001694), human papillomavirus-cand90 (NC-004104), human papillomavirus RTRX7 (NC-004761), human papillomavirus type 10 (NC-001576), human papillomavirus type 101 (NC-008189), human papillomavirus type 103 (NC-008188), human papillomavirus type 107 (NC-009239), human papillomavirus type 16 (NC-001526), human papillomavirus type 24 (NC-001683), human papillomavirus type 26 (NC-001583), human papillomavirus type 32 (NC-001586), human papillomavirus type 34 (NC-001587), human papillomavirus type 4 (NC-001457), human papillomavirus type 41 (NC-001354), human papillomavirus type 48 (NC-001690), human papillomavirus type 49 (NC-001591), human papillomavirus type 5 (NC-001531), human papillomavirus type 50 (NC-001691), human papillomavirus type 53 (NC-001593), human papillomavirus type 60 (NC-001693), human papillomavirus type 63 (NC-001458), human papillomavirus type 6b (NC-001355), human papillomavirus type 7 (NC-001595), human papillomavirus type 71 (NC-002644), human papillomavirus type 9 (NC-001596), human papillomavirus type 92 (NC-004500), human papillomavirus type 96 (NC-005134), human parainfluenza virus 1 (NC-003461), human parainfluenza virus 2 (NC-003443), human parainfluenza virus 3 (NC-001796), human parechovirus (NC-001897), human parvovirus 4 (NC-007018), human parvovirus B19 (NC-000883), human respiratory syncytial virus (NC-001781), human rhinovirus A (NC-001617), human rhinovirus B (NC-001490), human spumaretrovirus (NC-001795), human T-lymphotropic virus 1 (NC-001436), human T-lymphotropic virus 2 (NC-001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

EXAMPLES

Example 1—Synthesis of [4-({[3-({2-[3-(2,5-dioxo-2,5-dihydro-1H-pyrrol-1-yl) propanamido] ethyl}carbamoyl) quinoxalin-2-yl]oxy}methyl)-3,5-dimethoxyphenoxy]phosphonic acid (see Scheme 1)

A 2-hydroxyquinoxaline (HQ) hapten was modified with a caging group that could be released by alkaline phosphatase (AP), namely a caging group comprising a phosphatase enzyme substrate portion. Secondary anti-species antibodies (goat-anti-rabbit and goat-anti-mouse) were individually labeled with either the caged hapten (cHQ) or AP. Thus, any pair of rabbit and mouse primary antibodies could be tested to determine their proximity to each other. The caged HQ was synthesized according to the methodology set forth below and as illustrated in Scheme 1, which illustrates the preparation of caged HQ with a maleimide (MAL) reactive group for conjugation to antibodies (cHQ-MAL).

Scheme 3: Synthesis of [4-({[3-({2-[3-(2,5-dioxo-2,5-dihydro-1H-pyrrol-1-yl)propanamido]ethyl}carbamoyl)quinoxalin-2-yl]oxy}methyl)-3,5-dimethoxyphenoxy]phosphonic acid

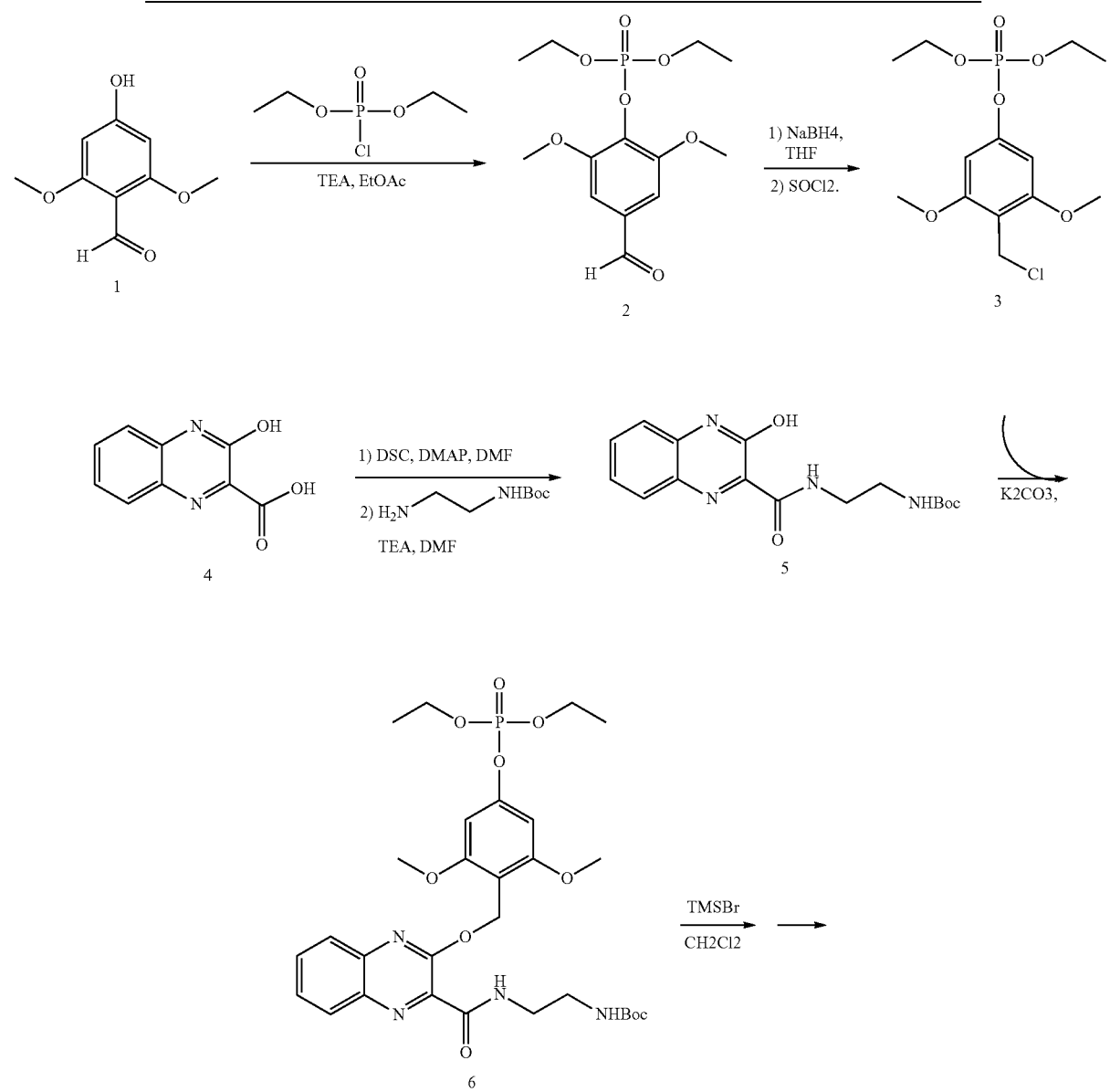

-continued

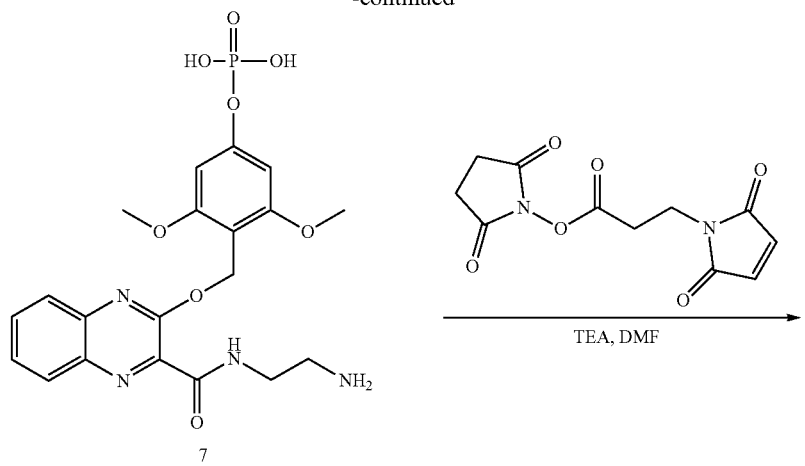

7

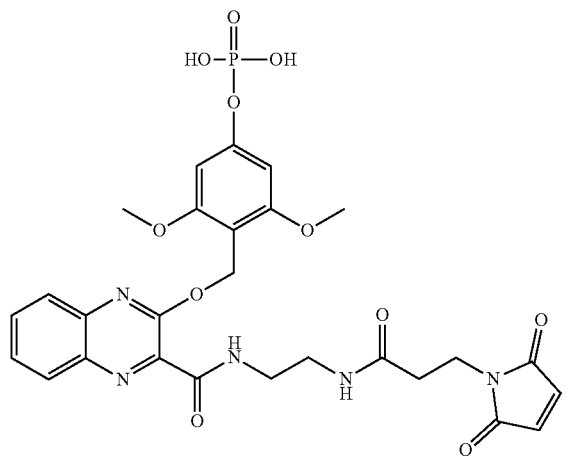

8

Compound 2. A soln. of 2,6-dimethoxy-4-hydroxybenzaldehyde (5.00 g, 27.4 mmol) and triethylamine (4.17 g, 5.74 mL, 41.2 mmol) in EtOAc (25 mL) was cooled to 0° C. in an ice bath in stirring. Diethyl chlorophosphate (4.73 g, 27.4 mmol) was then added dropwise over a period of 5 min. The reaction was allowed to warm to rt, followed by stirring at room temperature ("rt") for about 6 h (check HPLC to confirm reaction was greater than about 90% complete). The reaction mixture was quenched by addition of 1M HCl (100 mL) and the organic layer was separated and collected. An additional quantity of EtOAc (100 mL) was added and the organics were extracted with 1M HCl (2×100 mL), sat'd NaHCO$_3$ (3×100 mL) and brine (100 mL). The organic layer was dried over MgSO$_4$ and the solvents removed under reduced pressure to give compound 2 as a light brown viscous oil (7.95 g, 91% yield).

Compound 3. A soln. of compound 2 (7.95 g, 25.0 mmol) in THF (about 100 mL) was cooled to about 0° C. in an ice bath with stirring. NaBH$_4$ (1.42 g, 37.5 mmol) was crushed to fine powder with a mortar and pestle and was added portion-wise, followed by stirring at rt for about 4 h (check HPLC to confirm reaction completion). The reaction mixture was carefully quenched by addition of 1M HCl until bubbling ceased. The majority of the THF was then removed under reduced pressure. The resulting reaction mixture was extracted with EtOAc (3×100 mL). The organic layers were collected and combined, followed by washing with brine (about 100 mL) and drying over MgSO$_4$. The solvents were then removed under reduced pressure. The resulting light brown viscous oil was dissolved in dry CH$_2$Cl$_2$ (about 50 mL) followed by cooling to about 0° C. in an ice bath under an atmosphere of N$_2$ with stirring. SOCl$_2$ (4.46 g, 2.72 mL, 37.5 mmol) was then added dropwise over a period of about 5 min. The reaction mixture was allowed to warm to rt, followed by stirring at rt for an additional 1 h (check HPLC to confirm reaction completion). The reaction mixture was carefully quenched by addition of sat'd NaHCO$_3$ until bubbling ceased. The resulting reaction mixture was extracted with CH$_2$Cl$_2$ (3×100 mL). The organic layers were collected and combined, followed by washing with brine (100 mL) and drying over MgSO$_4$. The solvents were then removed under reduced pressure to give compound 3 as an off-white low melting solid (7.54 g, 89% yield).

Compound 5. 3-Hydroxy-2-quinoxalinecarboxylic acid (3.00 g, 15.8 mmol) was dissolved in DMF (50 mL), followed by addition of 4-dimethylaminopyridine (2.12 g, 17.4 mmol). The reaction mixture was stirred at rt until the 4-dimethylaminopyridine dissolved, at which point N,N'-disuccinimidyl carbonate (4.45 g, 17.4 mmol) was added. The reaction mixture was stirred at rt for 30 min (Check HPLC to confirm reaction completion. If the reaction was not complete, additional 0.1 eq portions of DSC were added until HPLC showed complete conversion). A soln. of N-Boc-ethylenediamine (3.04 g, 19.0 mmol) and triethylamine (2.40 g, 3.30 mL, 23.7 mmol) in DMF (10 mL) was then added, and the reaction was stirred at rt for 1 h (check HPLC for reaction completion). The reaction mixture was then poured onto a vigorously stirring soln. of 1M HCl (250 mL). The resulting precipitate was collected by vacuum filtration, washed several times with water, and dried under high-vacuum, giving compound 5 as a yellow solid (5.10 g, 97% yield).

Compound 6. Compound 5 (2.50 g, 7.52 mmol) was dissolved in DMF (50 mL), followed by addition of compound 3 (3.82 g, 11.3 mmol) and $K_2CO_3$ (5.20 g, 37.6 mmol). The reaction vessel was sealed and heated to 55° C. in an oil bath with vigorous stirring for 2 h (Check HPLC to confirm reaction completion. If the reaction was not complete, additional 0.1 eq portions of compound 3 were added until HPLC showed complete consumption of compound 5). The reaction mixture was filtered and the filtrate carefully quenched by addition of 1M HCl until bubbling ceased. The resulting reaction mixture was extracted with EtOAc (3×100 mL). The organic layers were collected and combined, followed by washing with brine (100 mL) and drying over $MgSO_4$. The solvents were then removed under reduced pressure to give a light yellow viscous oil. The resulting residue was purified by flash chromatography (Biotage Snap 50; hex: EA 1:0 to 1:4) to give compound 6 as a light yellow solid (3.15 g, 66% yield).

Compound 7. Compound 6 (3.15 g, 4.96 mmol) was dissolved in dry $CH_2Cl_2$ (25 mL) followed by dropwise addition of trimethylsilyl bromide (3.80 g, 3.28 mL, 24.8 mmol) over a period of 5 min. The vessel was sealed and the reaction mixture was stirred at rt for 16 h (check HPLC to confirm reaction completion). MeOH (25 mL) was then added and the solvents were removed under reduced pressure. The resulting solid was triturated with $CH_2Cl_2$ (100 mL) and the resulting solid was collected by vacuum filtration, giving compound 7 as a light yellow solid (2.06, 87% yield).

Compound 8. Compound 7 (2.06 g, 4.31 mmol) was suspended in DMF (10 mL), followed by addition of triethylamine (654 mg, 900 µL, 6.46 mmol) and finally 3-maleimidopropionic acid NHS ester (1.15 g, 4.31 mmol). The reaction vessel was sealed and the reaction mixture was vigorously stirred at room temperature for about 4 h (check HPLC to confirm reaction completion). The reaction mixture was diluted with MeOH (10 mL) and directly purified by prep RP-HPLC (0.05% TFA in $H_2O$: MeCN 99:1 to 5:95 over 40 min) in 5 portions to give compound 8 as a light yellow solid (1.95 g, 72% yield).

The maleimide functionalized HQ (cHQ-MAL) was conjugated to both goat-anti-rabbit and goat-anti-mouse IgG antibodies by two methodologies, via disulfide or lysine groups. In the disulfide method, the IgG was reduced by dithiothreitol (DTT) and then treated with an excess of cHQ-MAL. For the lysine method, the IgG was treated with an excess of Traut's reagent (2-iminothiolane hydrochloride) before adding an excess of cHQ-MAL. In both cases the conjugates were purified by size exclusion chromatography (SEC) and characterized by gel electrophoresis and UV-Vis spectroscopy.

Example 2—Confirmation of Blocking of Caging Group

Figure 5:
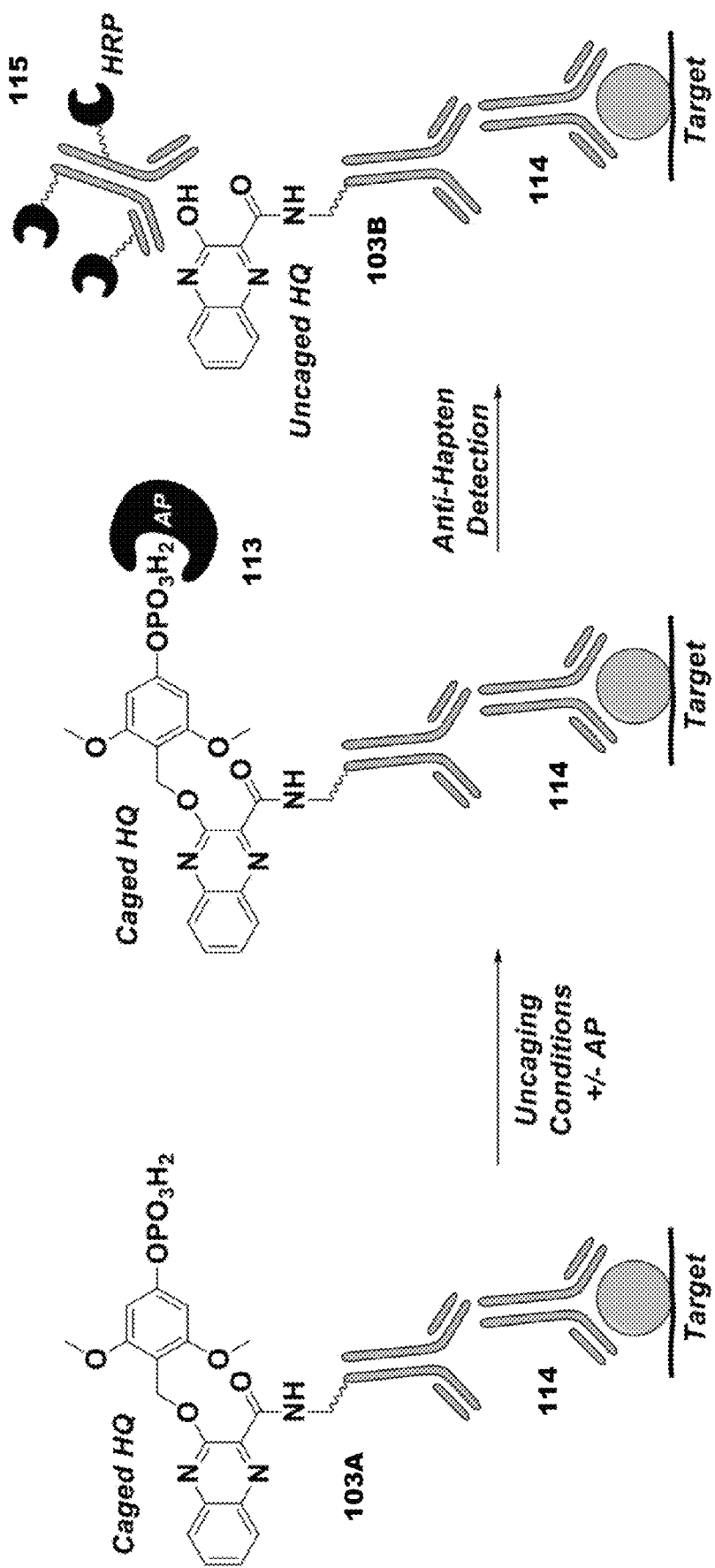
FIG. 5 is a schematic illustrating an embodiment of an IHC staining protocol where a single antigen is detected with a secondary antibody labeled with cHQ.

To confirm that the caging group of the caged hapten-antibody conjugate from Example 1 blocked an anti-hapten antibody from binding to the respective native (i.e. unmasked) hapten, the cHQ conjugate was tested with single IHC detection. FIG. 5 illustrates an IHC staining scheme where a single antigen (114) was detected with a secondary antibody conjugated to cHQ, i.e. a cHQ caged hapten-antibody conjugate (103A). Following introduction of the cHQ caged hapten-antibody conjugate (103A), an AP enzyme (i.e. free, unconjugated AP) (113) was introduced to unmask the hapten of the caged hapten-antibody conjugate. The resulting unmasked hapten (103B) was able to be recognized by an anti-hapten antibody (115). In some embodiments, the anti-hapten antibody (115) is conjugated to one or more enzymes (FIG. 5 illustrates the conjugation to 3 HRP enzymes).

Figure 6A:
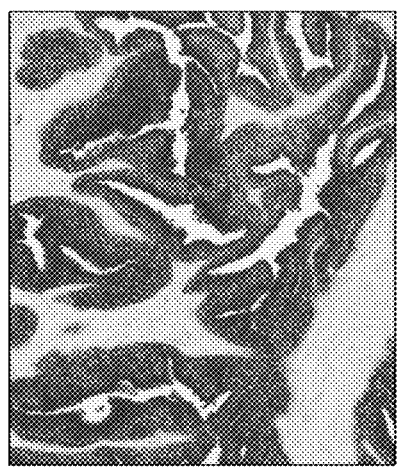
FIG. 6A is an image of the detection of PSA on prostate tissue with a secondary antibody labeled with cHQ and treatment with AP.
Figure 6B:
FIG. 6B is an additional image of the lack of detection of PSA on prostate tissue with a secondary antibody labeled with cHQ and no AP treatment (negative control).
Figure 6C:
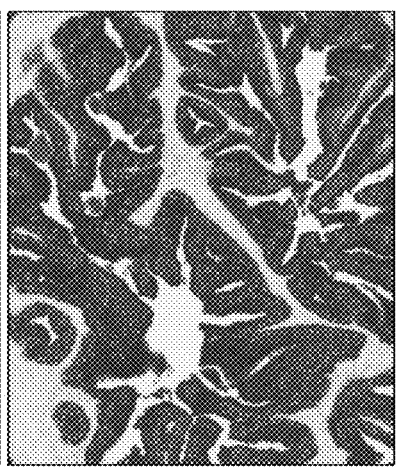
FIG. 6C is an additional image of the detection of PSA on prostate tissue with a secondary antibody labeled with native HQ.

With reference to FIGS. 6A-6C, mouse-anti-PSA bound to its target epitope on prostate tissue and was subsequently bound by goat-anti-mouse conjugated to cHQ (GAM-cHQ). Control slides (e.g. FIG. 6C) were generated using the goat-anti-mouse conjugated to uncaged HQ (GAM-HQ). Serial sections were exposed to two different conditions, namely (i) solutions with free (unconjugated) AP, pH adjust buffer and AP cofactors (magnesium salts); and (ii) solutions without AP, but with pH adjust buffer and AP cofactors (magnesium salts). FIG. 6A illustrates tissue treated with solution comprising AP; while FIG. 6B illustrates untreated tissue, i.e. solution without AP. FIG. 6C illustrates a control slide with a secondary antibody labeled with uncaged HQ. The sample tissues that were treated with AP under conditions favorable for the enzyme had the opportunity to allow unmasking of the caged hapten to occur (FIG. 6A). The negative sample tissues (no AP) did not have the opportunity for controlled unmasking to occur (FIG. 6B). These figures clearly illustrate that the slide that was treated with a GAM-cHQ but was not exposed to AP shows no positive staining (FIG. 6B). However, the slide that had both the GAM-cHQ and AP shows positive staining (FIG. 6A) and matches the non-caged control slide (FIG. 6C). This tested both the effectiveness of the caging group and its stability to the assay conditions.

Example 3—Measurement of Protein Proximity

A number of known positive and putative negative systems were investigated to test the ability of the disclosed conjugates to enable measurement of protein proximity. E-cadherin and beta-catenin were chosen as known positive systems since the biology dictates that these proteins are in close contact to each other in a normal cell. Her2/beta-catenin and EGFR/beta-catenin were chosen as pairs of protein that are in the same cell compartment (co-localized) but not expected to interact with each other (not proximal) and therefore should not generate signal in any proximity assay. The antibody pairs were also chosen so that there was one rabbit and one mouse primary antibody to allow the use of anti-species secondary detections.

With reference to the schemes outlined in FIGS. 2, 4, and 12, following introduction of the primary antibodies (e.g. an antibody conjugated to a hapten, a caged hapten-antibody conjugate, and an unmasking enzyme-antibody conjugate) and secondary antibodies (e.g. an anti-hapten antibody conjugated to an enzyme), and subsequent unmasking of the caged hapten, the uncaged HQ was detected with a mouse-anti-HQ conjugated to horseradish peroxidase (HRP). At this point either DAB (3,3'-diaminobenzidine), silver or a tyramide-chromogen could be used to visualize the proximity signal. A HRP/tyramide-hapten amplification step can also be included to boost the intensity (sensitivity) of the system (e.g. tyramide-HQ based optiView Amplification kit).

A general procedure for the automated caged hapten proximity assay was used to test FFPE cases: The slides were deparaffinized using a deparaffinizing solution of DISCOVERY EZ Prep (Ventana, p/n 950-100) or DISCOVERY Wash (Ventana, p/n 950-510). Heat induced epitope retrieval was performed on the slide using DISCOVERY CC1 (Ventana, p/n 950-124) at 95° C. for a time dependent on the identity of the two primary antibodies (0-92 minutes). DISCOVERY Inhibitor (Ventana, p/n 760-4840) was then applied to the slide to quench any endogenous peroxidase in the sample. A rabbit anti-target 1 antibody was co-incubated with a mouse anti-target 2 antibody at 37° C. for 16-32 minutes (dependent on the identities of the primary antibodies). Then a 30 µg/mL goat anti-mouse alkaline phosphatase conjugate was applied to the slide and incubated for 12 minutes. The slide was rinsed and a 20 µg/mL solution of the caged hapten goat anti-rabbit conjugate was applied to the slide for 16 minutes. After the incubation, a 500 mM tris buffer solution pH 10.0 and a 490 mM $MgCl_2$ solution were applied to the slide to enable the de-caging of the caged hapten. After the de-caging of the HQ, a mouse-anti-HQ HRP (Ventana, p/n 760-4820) conjugate was applied to the slide to bind the uncaged HQ. In some cases the Amp HQ tyramide amplification kit (Ventana, p/n 760-052) was used to help boost the signal intensity. Proximal proteins were visualized using the Chromomap DAB kit (Ventana, p/n 760-159), followed by counterstaining with Hematoxylin II (Ventana, p/n 790-2208) and Bluing Reagent (Ventana, p/n 760-2037).

Figures 7A, 7B, 7C:
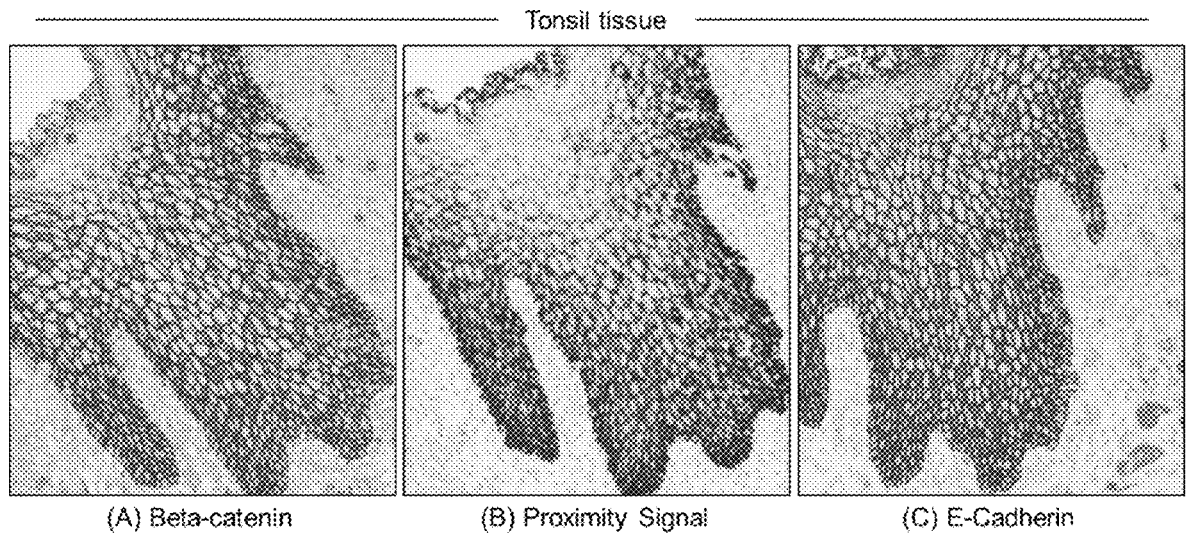
FIG. 7A is an image of total protein for Beta-Catenin as measured with DAB staining.
FIG. 7B is an image of proteins with positive proximity as measured with DAB staining.
FIG. 7C is an image of total protein for E-cadherin as measured with DAB staining.

FIGS. 7A-7C illustrate the results of this experiment and illustrate examples of proteins with positive proximity. FIG. 7A illustrates a single IHC DAB stain for Beta-Catenin (e.g. utilizing detection techniques comprising an antibody specific for Beta-Catenin, an anti-species antibody conjugated to an enzyme, and DAB). FIG. 7B illustrates a caged hapten proximity signal for Beta-Catenin and E-Cadherin (utilizing a caged hapten-antibody conjugate acted upon by an unmasking enzyme-antibody conjugate). FIG. 7C illustrates a single IHC DAB stain for E-Cadherin (e.g. utilizing detection techniques comprising an antibody specific for E-Cadherin, an anti-species antibody conjugated to an enzyme, and DAB).

Figures 8A, 8B, 8C:
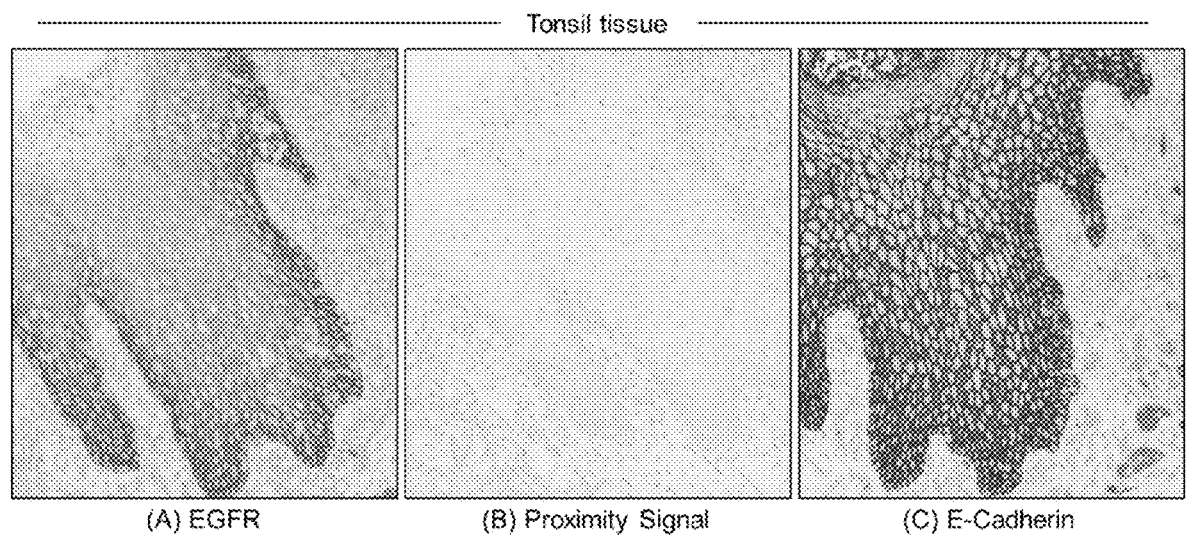
FIG. 8A is an image of total protein for EGFR as measured with DAB staining on FFPE tonsil tissue.
FIG. 8B is an image of co-localized proteins without proximity as measured with the absence of DAB staining on FFPE tonsil tissue.
FIG. 8C is an image of total protein for E-cadherin as measured with DAB staining on FFPE tonsil tissue.

FIGS. 8A-8C illustrates the results of IHC DAB staining and illustrate examples of co-localized proteins without proximity as detected with the conjugates and methods described herein. FIG. 8A illustrates a single IHC DAB stain for EGFR; FIG. 8B illustrates the absence of a caged hapten proximity signal for EGFR and E-Cadherin; and FIG. 8C illustrates a single IHC DAB stain for E-Cadherin.

In addition, FIGS. 9A and 9B illustrate examples of co-localized proteins with and without proximity on a different tissue type. Here, FIG. 9A illustrates positive caged hapten proximity signal for Beta-catenin and E-Cadherin, while FIG. 9B illustrates the lack of a caged hapten proximity signal for Beta-catenin and Her2. These examples illustrate that the assay is applicable to different tissue types, but generates the same type of results.

The signal intensity output from the above-described assays may be "dialed-in" a number of ways. The use of on-market signal amplification is easily applied to the presently disclosed technology and is believed to easily boost the signal (see, e.g. the amplification techniques described in U.S. Publication No. 2012/0171668, and PCT/EP2015/0533556, the disclosures of which are hereby incorporated by reference herein).

As illustrated in FIGS. 10A and 10B, the number of caged haptens conjugated to the secondary antibody also allows the sensitivity of the assay to be adjusted to fit a given system. In this example, FIG. 10A illustrates a sample labeled with goat-anti-rabbit and 4 (four) cHQ labels while FIG. 10B illustrates a sample labeled with goat-anti-rabbit and 9 (nine) cHQ labels. Here, the comparative increase in signal intensity is based on the increased number of caged haptens conjugated to the secondary antibody, where FIG. 10B clearly shows the increase in staining intensity as compared with FIG. 10A.

Example 4—Detection with Different HRP Systems

Different HRP systems providing different detectable signals (e.g. colors) were tested. For example, FIGS. 11A and 11B illustrate detection with silver (11A) and Tyramide-TAMRA (11B). Both systems were able to detect proximal protein targets in a sample.

Example 5—Multiplex Detection of Total Protein and Proximal Protein Signal

FIG. 12 is a schematic illustrating the multiplex detection of one total protein (Target 2, AP-Yellow) and the proximal protein signal (Target 1+Target 2, HRP-Silver). Any type of HRP detection system may be used to show the proximity signal and any AP detection system (e.g. naphthol phosphate/Fast Red, BCIP/NBT, quinone methide (QM)-chromogen) may be used to visualize the total protein.

The detection of proximal proteins utilizing HRP-DAB (FIG. 13A) and HRP-Silver with the addition of a total protein stain for one of the targets has also been demonstrated (FIG. 13B). These experiments were performed with E-cadherin and Beta-catenin on tonsil tissue. In addition, FIGS. 14A and 14B illustrate the use of different HRP detection systems to visualize the proximity signal along with total protein, utilizing an E-cadherin and Beta-catenin duel stain. FIG. 14A illustrates proximity detected with HRP-Purple and Beta-Catenin detected with AP-Yellow, while FIG. 13B illustrates proximity detected with HRP-Silver and Beta-Catenin detected with AP-Yellow.

Example 6—PD1/PD-L1

Binding of the ligand PD-L1 to its receptor PD-1 modulates the activation or inhibition of T-cells. Tumor cells can use this interaction to evade the immune system. Detection of a PD-L1/PD-1 complex may provide a better indication of the blockade status of the immune checkpoint within a tumor than simple measurement of either protein by itself.

Figure 16:
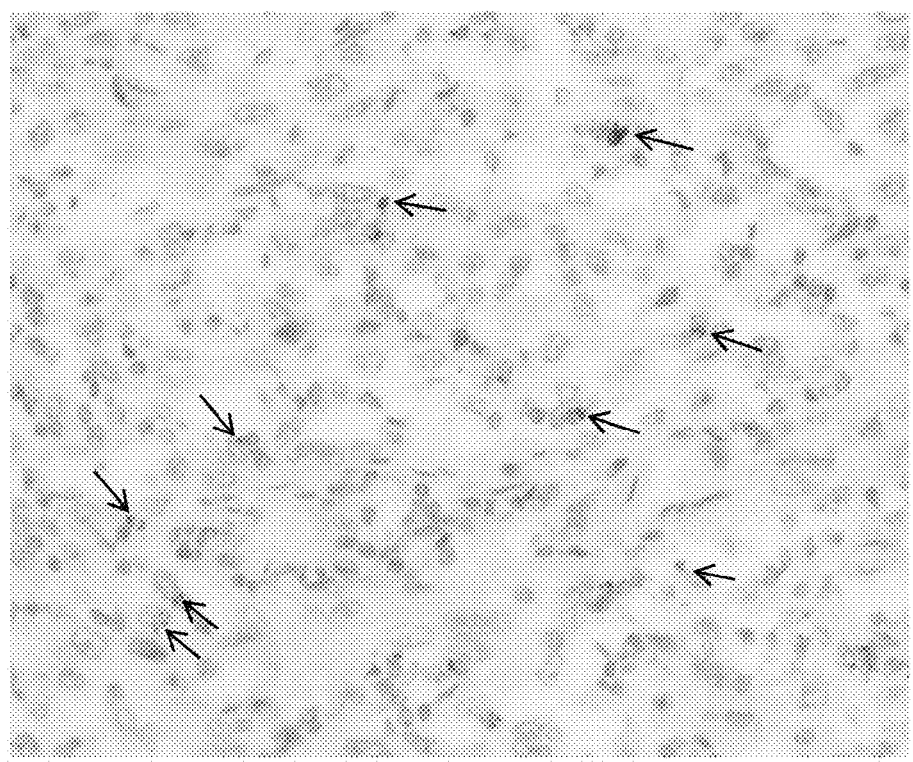
FIG. 16 provides an image of proximity signal detection of PD-1 and PD-L1 proteins as measured with HRP-Purple chromogen staining in a FFPE non-small cell lung cancer (NSCLC) case (Arrows=PD-L1/PD-1 proximity signal).

FIG. 16 illustrates a caged hapten proximity signal for PD-1 and PD-L1 (utilizing a caged hapten-antibody conjugate acted upon by an unmasking enzyme-antibody conjugate) in a NSCLC. The purple signal represents the detection of PD-L1/PD-1 complexes.

The caged hapten proximity assay was used to test FFPE cases of NSCLC and tonsil. The cases were run on the DISCOVERY ULTRA instrument, fully automated. The slides were deparaffinized using a deparaffinizing solution of DISCOVERY EZ Prep (Ventana, p/n 950-100) or DISCOVERY Wash (Ventana, p/n 950-510). Heat induced epitope retrieval was performed on the slide using DISCOVERY CC1 (Ventana, p/n 950-124) at 95° C. for 64 minutes. DISCOVERY Inhibitor (Ventana, p/n 760-4840) was then applied to the slide to quench any endogenous peroxidase in the sample. Rabbit anti-PD-L1 (SP263) (Ventana, p/n 790-4905) was co-incubated with a mouse anti-PD-1 (NAT105) (Ventana, p/n 760-4895) for 32 minutes at 37° C. For a negative control the mouse anti-PD-1 was omitted. For the remainder of the run, the slide was incubated at 37° C. A 30 µg/mL goat anti-mouse alkaline phosphatase conjugate was applied to the slide and incubated for 12 minutes. The slide was rinsed and a 20 µg/mL solution of the caged hapten goat anti-rabbit conjugate was applied to the slide for 16 minutes. After the incubation, a 500 mM tris buffer solution pH 10.0 and a 490 mM $MgCl_2$ solution were applied to the slide to enable the de-caging of the caged hapten. After the de-caging of the HQ, a mouse-anti-HQ HRP (Ventana, p/n 760-4820) conjugate was applied to the slide to bind the uncaged HQ. Proximal proteins were visualized using the DISCOVERY Purple kit (Ventana, p/n 760-229). The Amp HQ tyramide amplification kit (Ventana, p/n 760-052) was used to help boost the signal intensity when necessary.

Figure 17:
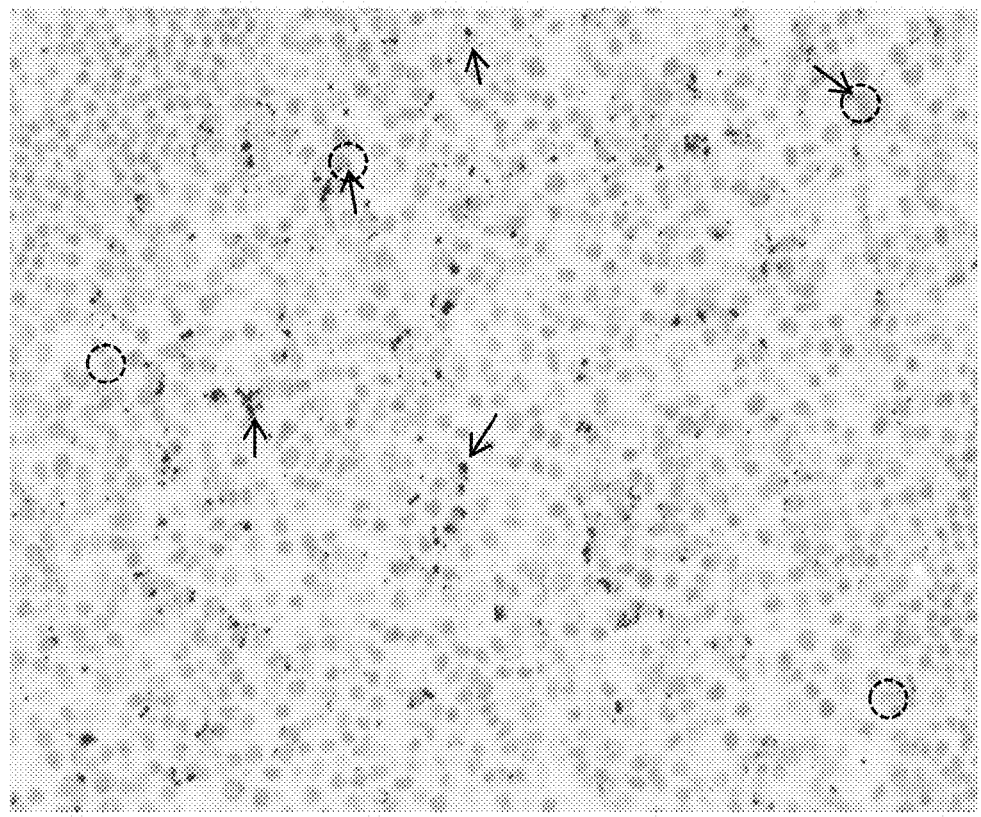
FIG. 17 provides an image of proximity signal detection of PD-1 and PD-L1 proteins as measured with HRP-Purple chromogen staining and total protein for PD-1 with AP-Yellow in FFPE tonsil (Arrows=PD-L1/PD-1 proximity signal; Dashed circles=PD-1 protein signal).

FIG. 17 illustrates a caged hapten proximity signal for PD-L1 and PD-1 along with the total protein detection for PD-1. After detection of proximal proteins with DISCOVERY Purple then the uncaging enzyme (alkaline phosphatase) was detected with DISCOVERY Yellow (Ventana, p/n 760-239) to visualize the PD-1 on the tissue.

Figure 18:
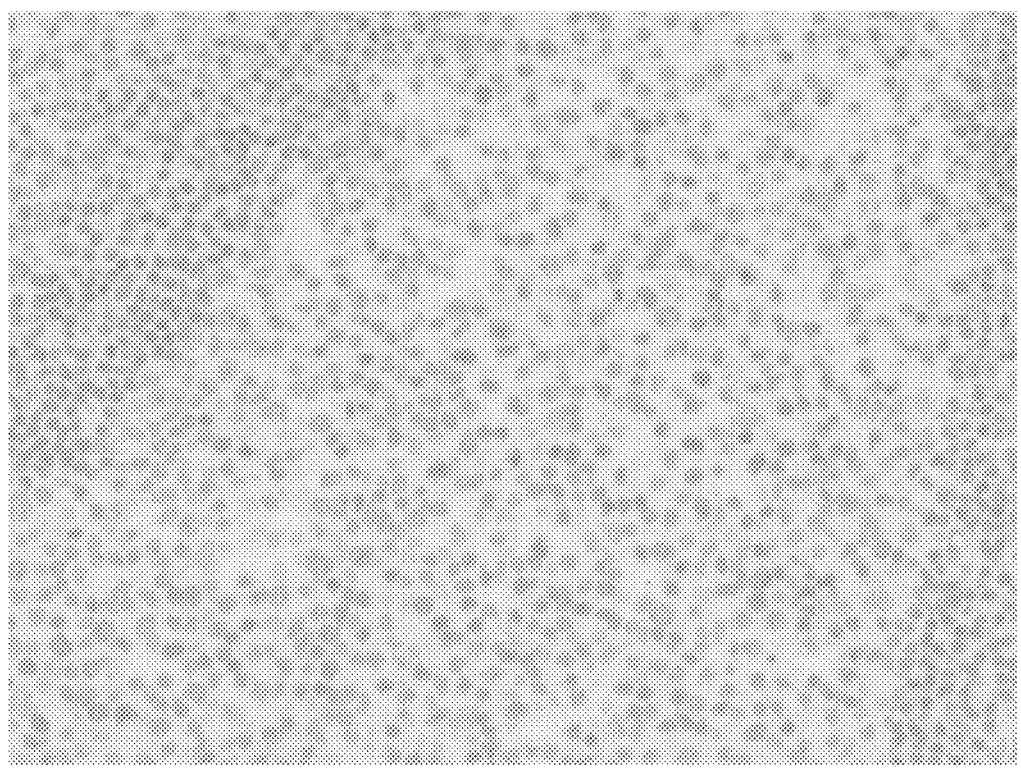
FIG. 18 provides an image of a negative control for proximity signal detection of PD-1 and PD-L1 proteins where the PD-1 antibody was omitted in FFPE tonsil and no signal was observed.

FIG. 18 illustrates a negative control for a caged hapten proximity signal for PD-L1 and PD-1 in tonsil tissue. The primary antibody for PD-1 was omitted from the assay. No signal was observed demonstrating the specificity of the detection reagents for the protein complex.

In all cases the slides were counterstained with Hematoxylin II (Ventana, p/n 790-2208) and Bluing Reagent (Ventana, p/n 760-2037).

Example 7—PD1/PD-L1 Combined with CD8

Figure 19:
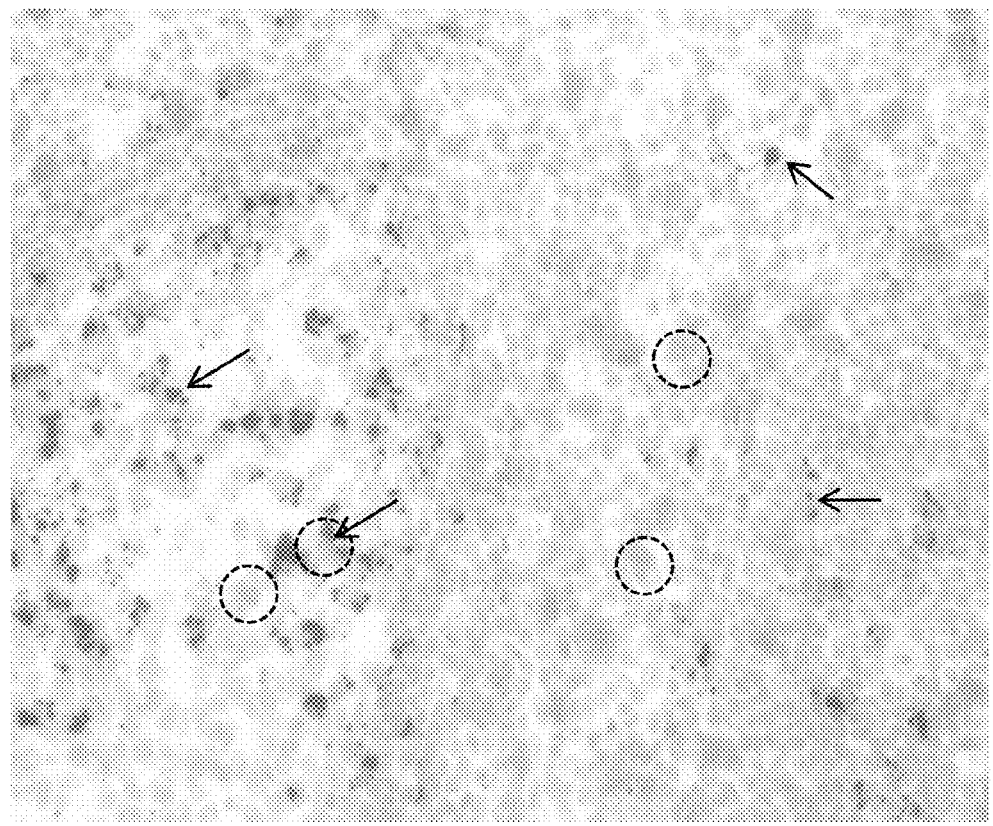
FIG. 19 provides an image of multiplex staining with proximity signal detection of PD-1 and PD-L1 proteins as measured with HRP-Purple chromogen staining and CD8 with AP-Yellow in FFPE tonsil (Arrows=PD-L1/PD-1 proximity signal; Dashed circles=CD8 protein signal).

FIG. 19 illustrates an example of combining the caged hapten proximity signal for PD-L1 and PD-1 with the subsequent detection of another biomarker in tonsil tissue. In this case CD8 was detected after the PD-L1/PD1 complex to generate an assay that visualized the CD8 cells that were involved in PD-L1/PD-1 interactions. For multiplexing, the PD-1 and PD-L1 proximity was first detected as previously described. The slides were heated to 90° C. for 8 minutes to assist in the elution of the previously bound primaries. Rabbit anti-CD8 (SP57) (Ventana, p/n 790-4460) was applied to the slide and incubated for 16 minutes at 37° C. The anti-CD8 was detected using UltraMap Rb AP (Ventana, p/n 760-4314) followed by the DISCOVERY Yellow chromogen. The slides were counterstained with Hematoxylin II (Ventana, p/n 790-2208) and Bluing Reagent (Ventana, p/n 760-2037).

Example 8—Her2/Her3

The caged hapten proximity assay was used to test FFPE cases of BT-474 cell lines. The cases were run on the DISCOVERY ULTRA instrument, fully automated. The slides were deparaffinized using a deparaffinizing solution of DISCOVERY EZ Prep (Ventana, p/n 950-100) or DISCOVERY Wash (Ventana, p/n 950-510). Heat induced epitope retrieval was performed on the slide using DISCOVERY CC1 (Ventana, p/n 950-124) at 95° C. for 64 minutes. DISCOVERY Inhibitor (Ventana, p/n 760-4840) was then applied to the slide to quench any endogenous peroxidase in the sample. Rabbit anti-Her2 (4B5) (Ventana, p/n 790-2991) was co-incubated with a mouse anti-Her3 (SPM738) (Spring, p/n E19260) for 32 minutes at 37° C. Then a 30 µg/mL goat anti-mouse alkaline phosphatase conjugate was applied to the slide and incubated for 12 minutes. The slide was rinsed and a 20 µg/mL solution of the caged hapten goat anti-rabbit conjugate was applied to the slide for 16 minutes. After the incubation, a 500 mM tris buffer solution pH 10.0 and a 490 mM $MgCl_2$ solution were applied to the slide to enable the de-caging of the caged hapten. After the de-caging of the HQ, a mouse-anti-HQ HRP (Ventana, p/n 760-4820) conjugate was applied to the slide to bind the uncaged HQ. The Amp HQ tyramide amplification kit (Ventana, p/n 760-052) was used to help boost the signal intensity. Proximal proteins were visualized using the Chromomap DAB kit (Ventana, p/n 760-159), followed by counterstaining with Hematoxylin II (Ventana, p/n 790-2208) and Bluing Reagent (Ventana, p/n 760-2037).

Figures 20A, 20B, 20C:
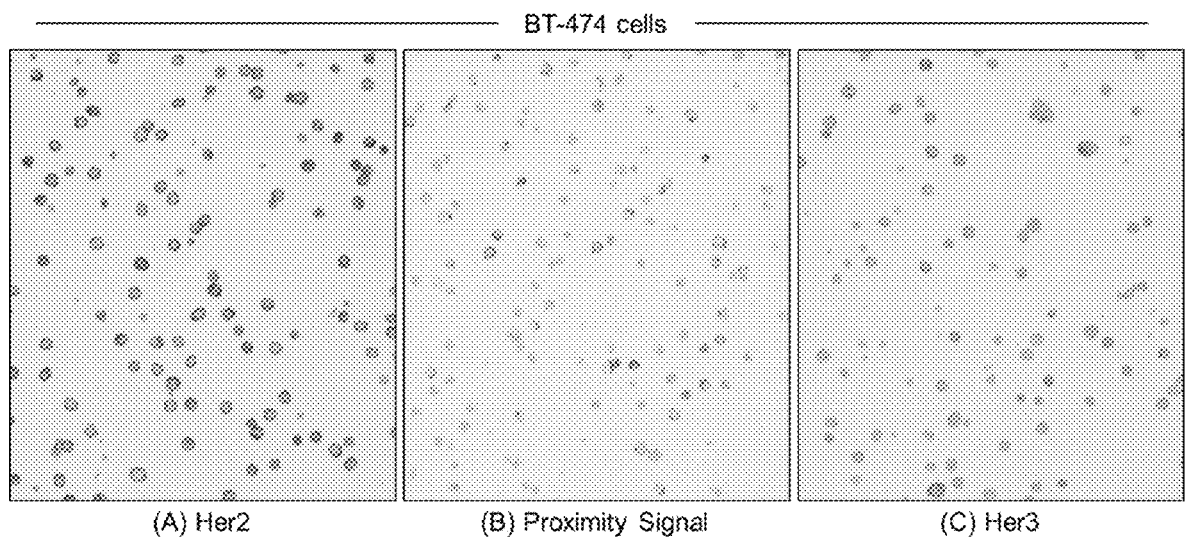
FIG. 20A is an image of total protein for Her2 as measured with DAB staining.
FIG. 20B is an image of Her2/Her3 proteins with positive proximity as measured with DAB staining.
FIG. 20C is an image of total protein for Her3 as measured with DAB staining.

FIGS. 20A-20C illustrate the results of this experiment and illustrate examples of proteins with positive proximity. FIG. 20A illustrates a single IHC DAB stain for Her2 (e.g. utilizing detection techniques comprising an antibody specific for Her2, an anti-species antibody conjugated to an enzyme, and DAB). FIG. 20B illustrates a caged hapten proximity signal for Her2 and Her3 (utilizing a caged hapten-antibody conjugate acted upon by an unmasking enzyme-antibody conjugate). FIG. 20C illustrates a single IHC DAB stain for Her3 (e.g. utilizing detection techniques comprising an antibody specific for Her3, an anti-species antibody conjugated to an enzyme, and DAB).

Various modifications of the invention, in addition to those described herein, will be apparent to those skilled in the art from the foregoing description. Such modifications are also intended to fall within the scope of the appended claims. For example, an "antibody" used in accordance with the present invention may be a whole antibody or a fragment of an antibody that is effective in binding to a desired target site. Also, when appropriate, an "antibody" of the present invention may be substituted with a targeting moiety (e.g., ligand peptide, small molecule, etc.). For example, if the tumor cell or the immune cell has a specific, differentiating and unique cell surface receptor, then a corresponding targeting moiety may be used in accordance with the present invention to differentiate tumor cells from immune cells.

The invention claimed is:

1. A method for analyzing a sample to determine whether a first target is proximal to a second target, the method comprising:
    (a) contacting the sample with an unmasking enzyme covalently coupled directly or indirectly to a first antibody forming to form an unmasking enzyme-antibody conjugate complex with the second target, wherein the first antibody is capable of specifically binding to the second target;
    (b) contacting the sample after step (a), with a caged hapten covalently coupled directly or indirectly to a second antibody to form a caged hapten-antibody conjugate complex with the first target, wherein the second antibody is capable of specifically binding to the first target, wherein the unmasking enzyme of the unmasking enzyme-antibody conjugate complex is capable of reacting with the caged hapten of the caged hapten-antibody conjugate complex, wherein if the first target is proximal to the second target the caged hapten of the caged hapten-antibody conjugate complex is unmasked by the unmasking enzyme of the unmasking enzyme-antibody conjugate complex to form an unmasked hapten-antibody conjugate complex;
    (c) contacting the sample after step (b), with first detection reagents specific to the unmasked hapten of the unmasked hapten-antibody conjugate complex, thereby labeling the unmasked hapten-antibody conjugate complex; and (d) detecting the labeled unmasked hapten-antibody conjugate complex if the unmasked hapten-antibody conjugate complex is formed.

2. The method of claim 1, wherein the first detection reagents comprise (i) a secondary antibody specific to the unmasked hapten of the unmasked hapten-antibody complex, the secondary antibody conjugated to a first enzyme such that the secondary antibody labels the unmasked hapten-antibody complex with the first enzyme; and (ii) a first substrate for the first enzyme.

3. The method of claim 2, wherein the first substrate is a chromogenic substrate or a fluorescent substrate.

4. The method of claim 1, wherein the first detection reagents include amplification components to label the unmasked hapten-antibody conjugate complex with a plurality of first reporter moieties.

5. The method of claim 4, wherein the plurality of first reporter moieties are haptens.

6. The method of claim 5, wherein the first detection reagents further comprise secondary antibodies specific to the plurality of first reporter moieties, each secondary antibody conjugated to a second reporter moiety.

7. The method of claim 5, wherein the second reporter moiety is selected from the group consisting of an amplification enzyme or a fluorophore.

8. The method of claim 7, wherein the second reporter moiety is an amplification enzyme and wherein the first detection reagents further comprise a first chromogenic substrate or a fluorescent substrate for the amplification enzyme.

9. The method of claim 2, further comprising contacting the sample with a second substrate specific for the unmasking enzyme of the unmasking enzyme-antibody conjugate complex and detecting signals corresponding to a product of a reaction between the second substrate and the unmasking enzyme.

10. A method for analyzing a sample to determine whether a first target is proximal to a second target, the method comprising:
(a) contacting the sample with an unmasking enzyme covalently coupled directly or indirectly to a first antibody to form an unmasking enzyme-antibody conjugate complex with the second target, wherein the first antibody is capable of specifically binding to the second target;
(b) contacting the sample after step (a), with a caged hapten covalently coupled directly or indirectly to a second antibody to form a caged hapten-antibody conjugate complex with the first target, wherein the caged hapten antibody second antibody is capable of specifically binding to the first target, wherein the unmasking enzyme of the unmasking enzyme-antibody conjugate complex is capable of reacting with the caged hapten of the caged hapten-antibody conjugate complex, wherein if the first target is proximal to the second target, the caged hapten of the caged hapten-antibody conjugate complex is unmasked to form an unmasked hapten-antibody conjugate complex;
(c) performing a signal amplification step after step (b) to specifically label the unmasked hapten of the unmasked hapten-antibody conjugate complex with a plurality of reporter moieties; and
(d) detecting the plurality of reporter moieties.

11. The method of claim 10, wherein the plurality of reporter moieties are haptens; and wherein the method further comprises introducing secondary antibodies specific to the plurality of first reporter moieties, wherein each secondary antibody is conjugated to a second reporter moiety.

12. The method of claim 11, wherein the second reporter moiety is an amplification enzyme and wherein the method further comprises introducing a chromogenic substrate or a fluorescent substrate for the amplification enzyme.

13. The method of claim 10, further comprising detecting a total amount of target in the sample.

14. A method for analyzing a sample to determine whether a first target is proximal to a second target, the method comprising:
(a) contacting the sample with an unmasking enzyme covalently coupled directly or indirectly to a first antibody to form an unmasking enzyme-antibody conjugate complex with the second target, wherein the first antibody is capable of specifically binding to the second target;
(b) contacting the sample after step (a), with a caged hapten covalently coupled directly or indirectly to a second antibody to form a caged hapten-antibody conjugate complex with the first target, wherein the second antibody is capable of specifically binding to the first target, wherein the unmasking enzyme of the unmasking enzyme-antibody conjugate complex is capable of reacting with the caged hapten of the caged hapten-antibody conjugate complex, wherein if the first target is proximal to the second target the unmasking enzyme of the unmasking enzyme-antibody conjugate complex reacts with the caged hapten of the caged hapten-antibody conjugate complex to form an unmasked hapten-antibody conjugate complex;
(c) contacting the sample after step (b), with first detection reagents capable of specifically labeling the unmasked hapten of the unmasked hapten-antibody conjugate complex or the first target; and
(d) detecting the labeled first target-unmasked hapten-antibody conjugate complex or the labeled first target.

15. The method of claim 14, wherein the reaction comprises changing the temperature of the sample.

16. The method of claim 14, wherein the reaction comprises altering a pH of the sample.

17. The method of claim 14, wherein the reaction comprises introducing one or more washing steps.

18. The method of claim 14, wherein the reaction comprises adding cofactors for the unmasking enzyme.

19. The method of claim 14, further comprising detecting a total amount of target in the sample.

* * * * *